(12) United States Patent
Nestor

(10) Patent No.: US 7,189,748 B2
(45) Date of Patent: Mar. 13, 2007

(54) COMPOUNDS AND METHODS FOR TREATING INSULIN RESISTANCE AND CARDIOMYOPATHY

(75) Inventor: John Nestor, Encinitas, CA (US)

(73) Assignee: Forbes Medi-Tech (Research), Inc., Seattle, WA (US)

( * ) Notice: Subject to any disclaimer, the term of this patent is extended or adjusted under 35 U.S.C. 154(b) by 0 days.

(21) Appl. No.: 11/248,491

(22) Filed: Oct. 12, 2005

(65) Prior Publication Data

US 2006/0079542 A1    Apr. 13, 2006

Related U.S. Application Data

(60) Provisional application No. 60/693,463, filed on Jun. 23, 2005, provisional application No. 60/664,919, filed on Mar. 23, 2005, provisional application No. 60/664,835, filed on Mar. 23, 2005, provisional application No. 60/617,911, filed on Oct. 12, 2004.

(51) Int. Cl.
  *A61K 31/41*   (2006.01)
  *A61K 31/4164* (2006.01)
  *C07D 233/56*  (2006.01)
  *C07D 271/10*  (2006.01)

(52) U.S. Cl. .................. 514/364; 514/400; 548/340.1; 548/136

(58) Field of Classification Search ................ 514/364, 514/529, 396; 548/335.1, 143
See application file for complete search history.

(56) References Cited

U.S. PATENT DOCUMENTS 5,068,247 A * 11/1991 Fujita et al. ................. 514/440
6,004,565 A    12/1999 Chiba et al.
6,667,025 B2   12/2003 Chiba et al.

OTHER PUBLICATIONS

Christensen, I.T. et al., "Excitatory Amino Acid Receptor Ligands. Synthesis and Biological Activity of 3-Isoxazolol Amino Acids Structurally Related to Homoibotenic Acid," J. Med. Chem., 1992, 35, 3512-3519.
Chen et al., "The identification of myriocin-binding proteins," Chemistry & Biology 1999, vol. 6, No. 4, pp. 221-235.
Clemens et al., "Synthesis of benzimidazole based analogues of sphingosine-1-phosphate: discovery of potent, subtype-selective S1P4 receptor agonists," Bioorganic & Medicinal Chemistry Letters 14 (2004) pp. 4903-4906.
Ding, W. and Yin, X., "Dissection of the multiple mechanisms of TNF-alpha-induced apoptosis in liver injury," J. Cell. Mol. Med. vol. 8, No. 4, 2004, pp. 445-454.
Hale et al., "Potent S1P receptor agonists replicate the pharmacologic actions of the novel immune modulator FTY720," Bioorganic & Medicinal Chemistry Letters 14 (2004) pp. 3351-3355.
Hale et al., "Synthesis, stereochemical determination and biochemical characterization of the enantiomeric phosphate esters of the novel immunosuppressive agent FTY720," Bioorganic & Medicinal Chemistry 12 (2004) pp. 4803-4897.
Hanada, K., "Serine palmitoyltransferase, a key enzyme of sphingolipid metabolism," Biochimica et Biophysica Acta 1632 (2003) pp. 16-30.
Hojjati et al., "Effect of Myriocin on Plasma Sphingolipid Metabolism and Atherosclerosis in apoE-deficient Mice," J. of Biol. Chem. vol. 280, No. 11, Mar. 18, 2005, pp. 10284-10289.
Fujita et al., "Potent Immunosuppressants, 2-Alkyl-2-aminopropane-1,3-diols," J. Med. Chem., 1996, 39:4451-4459.
Kiuchi et al., "Synthesis and Immunosuppressive Activity of 2-Substituted 2-Aminopropane-1,3-diols and 2-Aminoethanols," J. Med. Chem., 2000, 43:2946-2961.
Kobayashi et al., "Catalytic Asymmetric Synthesis of Antifungal Sphingofungins and Their Biological Activity as Potent Inhibitors of Serine Palmitoyltransferase (SPT)," J. Am. Chem. Soc. 1998, 120:908-919.
Maedler et al., "Monounsaturated Fatty Acids Prevent the Deleterious Effects of Palmitate and High Glucose on Human Pancreatic β-Cell Turnover and Function," Diabetes, vol. 52, Mar. 2003, pp. 726-733.
Nakamura et al., "Dual Roles of Sphingolipids in Signaling of the Escape from and Onset of Apoptosis in a Mouse Cytotoxic T-cell Line, CTLL-2," J. of Biol. Chem., vol. 271, No. 3, Jan. 19, 1996, pp. 1255-1257.
Park et al., "Inhibition of Sphingomyelin Synthesis Reduces Atherogenesis in Apolipoprotein E-Knockout Mice," Circulation, Nov. 30, 2004, pp. 3465-3471, DOI: 10.116/01.CIR.0000148370.60535.22.
Schmitz-Peiffer et al., "Ceramide Generation is Sufficient to Account for the Inhibition of the Insulin-stimulated PKB Pathway in C2C12 Skeletal Muscle Cells Pretreated with Palmitate," J. of Biol. Chem., vol. 274, No. 34, Aug. 20, 1999, pp. 24202-24210.
Seebach et al., "Stereoselective Alkylation at C(alpha) of Serine, Glyceric Acid, Threonine, and Tartaric Acid Involving Heterocyclic Enolates with Exocyclic Double Bonds," Helvetica Chimica Acta, vol. 70 (1987), pp. 1194-1216.
Seidel et al., "Iron-Catalyzed Cross-Coupling Reactions, A Scalable Synthesis of the Immunosuppressive Agent FTY720," J. Org. Chem. 2004, 69:3950-3952.

(Continued)

*Primary Examiner*—Joseph K. McKane
*Assistant Examiner*—Yong Chu
(74) *Attorney, Agent, or Firm*—Wilson Sonsini Goodrich & Rosati

(57) ABSTRACT

Novel compounds, compositions comprising compounds, and methods for methods for preparing and using compounds are described herein. Methods of treating or ameliorating various conditions, including insulin resistance, pancreatic beta cell apoptosis, obesity, pro-thrombotic conditions, myocardial infarction, hypertension, dyslipidemia, manifestations of Syndrome X, congestive heart failure, inflammatory disease of the cardiovascular system, atherosclerosis, sepsis, type 1 diabetes, liver damage, and cachexia, by administering compounds described herein. Compounds presented herein may be used to modulate serine palmitoyl transferase activity.

26 Claims, No Drawings

OTHER PUBLICATIONS

Shimabukuro et al., "Fatty acid-induced β cell apoptosis: A link between obesity and diabetes," PNAS USA vol. 95, pp. 2498-2502, Mar. 1998.

Shimabukuro et al., "Lipoapoptosis in Beta-cells of Obese Prediabetic fa/fa Rats," J. of Biol. Chem. vol. 273, No. 49, Dec. 4, 1998, pp. 32487-32490.

Smedes, F., "Determination of total lipid using non-chlorinated solvents," Analyst, 1999, 124:1711-1718.

Sweet et al., "Systematic screening of potential β-cell imaging agents," Biochemical and Biophysical Res. Communications 314 (2004) pp. 976-983.

Ayasolla, K. et al., "Inflammatory Mediator and β-Amyloid (25-35)-Induced Ceramide Generation and iNOA Expression are Inhibited by Vitamin E," Free Radical Biol. & Medicine, vol. 37, No. 3, pp. 325-338, 2004.

Beattie, G.M. et al., "Protection From Cell Death in Cultured Human Fetal Pancreatic Cells," Cell Transplantation, vol. 9, pp. 431-438, 2000.

Beattie, G.M. et al., "Trehalose: A Cryoprotectant That Enhances Recovery and Preserves Function of Human Pancreatic Islets After Long-Term Storage," Diabetes 46:519-523(1997).

Bell, D.S.H. and Ovalle, F., "Outcomes of initiation of therapy with once-daily combination of a thiazolidinedione and a biguanide at an early stage of type 2 diabetes," Diabetes, Obesity and Metabolism 6:363-366 (2004).

Benjamins, J.A. et al., "Protection of Mature Oligodendrocytes by Inhibitors of Caspases and Calpains," Neurochemical Res., vol. 28, No. 1, Jan. 2003, pp. 143-152.

Bennett, J.W. and Klich, M., "Mytotoxins," Clinical Microbiol. Reviews, vol. 16, No. 3, Jul. 2003, pp. 497-516.

Buse, J.B. et al., "The effects of oral anti-hyperglycaemic medications on serum lipid profiles in patients with type 2 diabetes," Diabetes, Obesity and Metabolism 6:133-156 (2004).

Canbay, A. et al., "The Caspase Inhibitor IDN-6556 Attenuates Hepatic Injury and Fibrosis in the Bile Duct Ligated Mouse," J. of Pharmacological and Experimental Therapeutics 308(3):1191-1196 (2004).

Coroneos, E. et al., "Sphingolipid metabolites differentially regulate extracellular signal-regulated kinase and stress-activated protein kinase cascades," Biochem J (1996) 316, pp. 13-17.

Creutzfeldt, W., "The [pre-] history of the incretin concept," Regulatory Peptides 128:87-91 (2005).

Cutler, R.G. et al., "Involvement of oxidative stress-induced abnormalities in ceramide and cholesterol metabolism in brain aging and Alzheimer's disease," PNAS, vol. 101, No. 7, pp. 2070-2075 (Feb. 17, 2004).

Diani, A.R. et al., "Pioglitazone preserves pancreatic islet structure and insulin secretory function in three murine models of type 2 diabetes," Am. J. Physiol.

Durand, P. et al., "A New Efficient Synthesis of the Immunosuppressive Agent FTY-720," Synthesis, 2000, No. 4, pp. 505-506.

Eitel, K. et al., "Different role of saturated and unsatured fatty acids in β-cell apoptosis," Biochem. and Biophys. Res. Comm. 299 (2002)853-856.

Esmon, Charles T., "Crosstalk between inflammation and thrombosis," Maturitas 47 (2004) 305-314.

Filipsson, K. et al., "Pituitary Adenylate Cyclase-Activating Polypeptide Stimulates Insulin and Glucagon Secretion in Humans," J. of Clinical Endocrinology and Metabolism 82(9):3093-3098 (1997).

Frost, R.A. and Lang, C.H., "Skeletal muscle cytokines: regulation by pathogen-associated molecules and catabolic hormones," Curr. Op. Clin. Nutrition and Metabolic Care 2005, 8:255-263.

Gavrieli, Y. et al., "Identification of Programmed Cell Death In Situ via Specific Labeling of Nuclear DNA Fragmentation," J. Cell Biol. 119:493-501 (Nov. 1992).

Greene, T. and Wutts, P.G.M., *Protective Groups in Organic Synthesis*, 3rd Ed., 1999, John Wiley & Sons, New York.

Harwood, H. J. Jr., "Acetyl-CoA carboxylase inhibition for the treatment of metabolic syndrome," Curr. Opin. in Investigational Drugs 5(3):283-289 (2004).

Hoglen, N.C. et al., "Characterization of IDN-6556 (3- {2-(2-tert-Butyl-phenylaminooxalyl)-amino]-propionylamino}-4-oxo-5-(2,3,4,5,6-tetrafluoro-phenoxy)-pentanoic Acid): a Liver-Targeted Caspase Inhibitor," J. of Pharmacology and Experimental Therapeutics 309(2):634-640 (2003).

Ilieva, A. et al., "Pancreatic islet cell survival following islet isolation: the role of cellular interactions in the pancreas," J. Endocrinology 161:357-364 (1999).

Kajita, K. et al., "TNA alpha reduces the expression of peroxisome proliferator-activated receptor y (PPARy) via the production of ceramide and activation of atypical PKC," Diabetes Res. Clin. Practice, 66 Suppl. (2004) S79-S83.

Kanzler, S. and Galle, P., "Apoptosis and the liver," Semin. Cancer Biol. 10(3):173-184 (2000).

Knudsen, L.B., "Glucagon-like Peptide 1: The Basis for a New Class of Treatment for Type 2 Diabetes," J. Med. Chem. 47:4128-4134 (2004).

Krstenansky, J.L. et al., Probing Proteinase Active Sites Using Oriented Peptide Mixture Libraries—ADAM-10:, Letters in Drug Design and Discovery 1:6-13 (2004).

Larock, R.C. *Comprehensive Organic Transformations*, 2nd ed., John Wiley & Sons, New York 1999.

Lee, C., Olson, P. and Evans, R., "Minireview: Lipid Metabolism, Metabolic Diseases and Peroxisome Proliferator-Activated Receptors," Endocrinology 144(6):2201-2207 (2003).

Matsumoto, S. et al., "A comparative evaluation of culture conditions for short-term maintenance (<24h) of human islets isolated using the Edmonton protocol," Cell Tissue Banking 4:85-93 (2003).

McTiernan, C.F. and Feldman, A., "The Role of Tumor Necrosis Factor Alpha in the Pathophysiology of Congestive Heart Failure," Curr. Cardiol. Rep. 2(3):189-197 (2000).

Merrill, A. et al., "Quantitation of Free Sphingosine in Liver by High-Performance Liquid Chromatography," Analytical Biochem. 171:373-381 (1988).

Meyer, S. and De Groot, H., "Cycloserine and threo-dihydrosphingosine inhibit TNF-alpha-induced cytotoxicity: evidence of importance of de novo ceramide synthesis in TNF-alpha signaling," Biochim Biophys Acta 1643 (2003) 1-4.

Nestor, J., "Peptide and Protein Drugs: Issues and Solutions", in *Comprehensive Medicinal Chemistry II*, vol. 2, Ch. 14 Proofs; Moos, W. Ed., in press 2006, Elsevier, London.

Nolte, M.S., MD and Karam, J.H., MD., "Pancreatic Hormones & Antidiabetic Drugs," *Basic & Clinical Pharmacology*, 8th ed., Bertram G. Katzung, MD, PhD, ed., Lange Medical Books/McGraw Hill, New York 2001, Chapter 41, pp. 711-734.

Nourparvar, A. et al., "Novel strategies for the pharmacological management of type 2 diabetes," Trends in Pharmacological Science25:86-91 (2004).

Oberholzer, J. et al., "Human Islet Transplantation: Lessons from 13 Autologous and 13 Allogeneic Transplantations," Transplantation 69:1115-1123 (2000).

O'Donnell, M. et al., "Ro25-1553: A Novel, Long-Acting Vasoactive Intestinal Peptide Agonist. Part I: In Vitro and In Vivo Bronchodilator Studies," J. of Pharmacology and Experimental Therapeutics 270:1282-1288 (1994).

Ohgawara, H. et al., "Survival and B-Cell Function of Neonatal Pig Pancreatic Islet-Like Cell Clusters in an Extracellular Matrix," Pancrease 6:625-30 (1991).

Oishi, T. et al., "Stereoselective total synthesis of (+)-myriocin from D-mannose," Chem. Commun., 2001, 1932-1933.

Otonkoski, T. et al., "Differentiation and Maturation of Porcine Fetal Islet Cells In Vitro and After Transplantation," Transplantation 68:1674-1683 (1999).

Paraskevas, S. et al., "Cell Loss in Isolated Human Islets Occurs by Apoptosis," Pancreas 20(3):270-276 (2000).

Pileggi, A. et al., "Protecting Pancreatic β-Cells," IUBMB Life 56:387-394 (2004).

Pipik, B. et al., "A Preferred Synthesis of 1,2,4-Oxadiazoles," Synth. Commun. 34(10):1863-1870 (2004).

Pladevall, M. et al., "A Single Factor Underlies the Metabolic Syndrome," Diabetes Care 29(1):113-122 (2006).

Rall, L.C. and Roubenoff, R., "Rheumatoid cachexia: metabolic abnormalities, mechanisms and interventions,"Rheumatology 2004;43:1219-1223.

Reed, J.C., "Apoptosis-Based Therapies," Nature Rev. Drug Discovery 1:111-121 (2002).

Rosenberg, L. et al., "Structural and functional changes resulting from islet isolation lead to islet cell death," Surgery 126(2):393-398 (1999).

Rother, K. and Harlan, D.M., "Challenges facing islet transplantation for the treatment of type 1 diabetes mellitus," J. Clin. Investigation 2004;114:877-883.

Ryan, E. et al., "Clinical Outcomes and Insulin Secretion After Islet Transplantation With The Edmonton Protocol," Diabetes 50:710-719 (2001).

Sauerwald, T.M. et al., "Study of Capase Inhibitors for Limiting Death in Mammalian Cell Culture," Biotechnol. Bioeng. 81:329-340 (2003).

Sawada, M. et al., "Molecular mechanisms of TNF-alpha-induced ceramide formation in human glioma cells: P53 -mediated oxidant stress-dependent and-independent pathways," Cell Death Differentiation 11:997-1008 (2004).

Shi, Y., "Capase activation, inhibition, and reactivation: A mechanistic view," Protein Science 13:1979-1987 (2004).

Shinoda, J. et al., "Effect of Ceramide on Interleukin-6 Synthesis in Osteoblast-Like Cells," Cell Signal. 11:435-441 (1999).

Spector, A. et al., "Analysis of Long-Chain Free Fatty Acid Binding to Bovine Serum Albumin by Determination of Stepwise Equilibrium Constants," Biochem 10:3229-3232 (1971).

Stack, J.H. et al., "IL-Converting Enzyme/Capsase-1 Inhibitor VX-765 Blocks the Hypersensitive Response to an Inflammatory Stimulus in Monocytes from Familial Cold Autoinflammatory Syndrome Patients," J. of Immunol. 175:2630-2634 (2005).

Talanian, R. and Allen, H.J., "Roles of Caspases in Inflammation and Apoptosis: Prospects as Drug Discovery Targets," *Annual Reports in Medicinal Chemistry*, James Bristol, ed., Academic Press, vol. 33, Chapter 27, pp. 273-282, 1998.

Thorkildsen, C. et al., "Glucagon-Like Peptide 1 Receptor Agonist ZP10A Increases Insulin mRNA Expression and Prevents Diabetic Progression in db/db Mice," J. of Pharmacology and Experimental Therapeutics 307(2):490-496 (2003).

Tisdale, M.J., "Cancer cachexia," Langenbecks Arch. Surg.(2004) 389:299-305.

Tsutsumi, M. et al., "A Potent and Highly Selective VPAC2 Agonist Enhances Glucose-Induced Insulin Release and Glucose Disposal," Diabetes 51:1453-1460 (2002).

Wang, Y.F. et al., "Lipase-Catalyzed Irreversible Transesterifications Using Enol Esters as Acylating Reagents: Preparative Enantio- and Regioselective Synthesis of Alcohols, Glycerol Derivatives, Sugars, and Organometallics," J. Am. Chem. Soc. 110:7200-7205 (1988).

Wencker, D. et al., "A mechanistic role for cardiac myocite apoptosis in heart failure," J. Clin. Investigation 111:1497-1504 (2003).

Yang, B. et al., "Inhibitors Directed towards Caspase-1 and -3 Arc Less Effective than Pan Caspase Inhibition in Preventing Renal Proximal Tubular Cell Apoptosis," Nephron Exp Nephrol 2004; 96: e39-e51.

Yung, S.L. et al., "Generation of Highly Selective VPAC2 Receptor Agonists by High Throughput Mutagenesis of Vasoactive Intestinal Peptide and Pituitary Adenylate Cyclase-activating Peptide," J. of Biol. Chem. 278(12):10273-10281 (2003).

Zimmet, P. et al., "Global and societal implications of the diabetes epidemic," Nature 414:783-787 (2001).

* cited by examiner

COMPOUNDS AND METHODS FOR TREATING INSULIN RESISTANCE AND CARDIOMYOPATHY

CROSS-REFERENCE TO RELATED APPLICATIONS

This application claims benefit of the following provisional applications: 60/617,911 filed on Oct. 12, 2004, 60/664,835 filed on Mar. 23, 2005, 60/664,919 filed on Mar. 23, 2005, and 60/693,463 filed on Jun. 23, 2005. The contents of these provisional applications are herein incorporated by reference in their entireties.

BACKGROUND

All publications mentioned herein are cited for the purpose of familiarizing the reader with the background of the invention. Nothing herein is to be construed as an admission that these references are prior art in relation to the inventions described herein.

Although Type 2 Diabetes (i.e., T2D, diabetes mellitus, non-insulin dependent diabetes mellitus, adult onset diabetes) is frequently thought of as a disease caused by high blood sugar, modern thinking has regarded blood glucose levels as mainly a symptom of an underlying disease related to dysregulated fat metabolism. Thus high fatty acid levels lead to a range of lipotoxicities: insulin resistance, pancreatic beta cell apoptosis, and a disorder termed "metabolic syndrome." Insulin resistance can be detected by the following indications: as an increased level of blood insulin, increased blood levels of glucose in response to oral glucose tolerance test (OGTT), decreased levels of phosphorylated protein kinase B (AKT) in response to insulin administration, and the like. Insulin resistance may be caused by decreased sensitivity of the insulin receptor-related signaling system in cells and/or by loss of beta cells in the pancreas through apoptosis. There is also evidence that insulin resistance can be characterized as having an underlying inflammatory component.

Sedentary lifestyle and obesity have contributed to the increased occurrence of T2D. Therapeutic intervention has been aimed at people with impaired glucose tolerance (IGT). IGT is defined as hyperglycaemia (with glucose values intermediate between normal and diabetes) following a glucose load, and affects at least 200 million people worldwide. People afflicted with IGT possess a higher future risk than the general population for developing diabetes. Approximately 40% of people with IGT progress to diabetes in 5–10 years, but some revert to normal or remain IGT.

Moreover, people with IGT also have a heightened risk of developing cardiovascular disease, such as hypertension, dyslipidaemia and central obesity. Thus, the diagnosis of IGT, particularly in apparently healthy and ambulatory individuals, has important prognostic implications. For a more detailed review, see Zimmet P, et al., Nature, 414:783–7 (2001), the disclosure of which is incorporated herein by reference.

Recently, impaired fasting glucose (IFG) was introduced as another category of abnormal glucose metabolism. IGF is defined on the basis of fasting glucose concentration and, like IGT, it is also associated with risk of cardiovascular disease and future diabetes.

T2D may be caused by a variety of factors. Additionally, the disease also manifests heterogeneous symptoms. Previously, T2D was regarded as a relatively distinct disease entity, but current understanding has revealed that T2D (and its associated hyperglycaemia or dysglycaemia) is often a manifestation of a much broader underlying disorder, which includes the metabolic syndrome. This syndrome is sometimes referred to as Syndrome X, and is a cluster of cardiovascular disease risk factors that, in addition to glucose intolerance, includes hyperinsulinaemia, dyslipidaemia, hypertension, visceral obesity, hypercoagulability, and micro albuminuria.

Recent understanding of the factors leading to T2D has influenced contemporary therapy for the disease. More aggressive approaches to treating hyperglycaemia as well as other risk factors such as hypertension, dyslipidaemia and central obesity in type 2 diabetics have been pursued. In addition, more simplistic and comprehensive screening of at-risk individuals has been advocated by health organizations, such as the American Diabetes Association.

Ceramide has been reported as showing activity in some of the factors relating to T2D, such as insulin resistance and beta cell apoptosis. For example, Schimitz-Pfiffer et al. report that feeding cells with palmitic acid or ceramide leads to insulin resistance (Schimitz-Pfiffer C., et al., J. Biol. Chem., 274: 24202–10 (1999)). Increased levels of palmitic acid in cells leads directly to increased levels of ceramide through an increase in levels of Palmitoyl-CoA which feeds into the de novo ceramide synthesis pathway. Studies suggest that de novo ceramide synthesis of ceramide is an important factor, since inhibition of ceramide synthase with fuminosin blocks beta cell apoptosis (Shimabukuro M., et al., Proc. Nati. Acad. Sci. USA, 95: 2498–2502 (1998)). Similarly, it has been recognized that the enzyme involved in the rate limiting step for the de novo pathway for ceramide synthase, serine palmitoyl transferase (SPT), may be a viable target for blockade of beta cell apoptosis. For example, Shimabukuro et al. report that inhibition of SPT with cycloserine has a partial beta cell protective effect (~50% activity) in the diabetic Zucker fatty rat model (Shimabukuro, et al., J. Biol. Chem., 273: 32487–90 (1998), the disclosure of which is incorporated herein by reference).

A well known proinflammatory signal, Tumor Necrosis Factor alpha (TNF), has been shown to raise ceramide levels in cells in culture (Sawada, M, et al., Cell Death Differ., 11:997–1008 (2004); Meyer, S G, et al., Biochim Biophys Acta. 1643(1–3):1–4(2003)). TNF administration reduces PPAR-gamma levels in adipocytes and this has been shown to implicate ceramide (Kajita, K, et al. Diabetes. Res. Clin. Pract., 66 Suppl 1: S79–83 (2004)). TNF also induces apoptosis in liver cells and has been implicated in injury due to viral hepatitis, alcoholism, ischemia, and fulminant hepatic failure (Ding, W X and Yin, X M, J. Cell. Mol. Med. 8:445–54 (2004); Kanzler S., et al. Semin Cancer Biol. 10(3):173–84 (2000)). Similarly, TNF and IL-6 are implicated in cachexia, another syndrome with strong evidence of an inflammatory component, implicating ceramide as an effector. It is known that atherosclerosis has an inflammatory component. Induction of oxidative stress by amyloid involves induction of a cascade that increases ceramide levels in neuronal cells (Ayasolla K., et al., Free Radic. Biol. Med., 37(3):325–38(2004)). Thus altered ceramide levels may be causative in dementias such as Alzheimer's disease and HIV dementia and modulation of these levels with an SPT inhibitor is conceived as having promise as a treatment (Cutler R G, et al., Proc Natl. Acad. Sci., 101:2070–5 (2004)). TNF is known to be involved in sepsis and insulin has protective effects (Esmon, C T. Crosstalk between inflammation and thrombosis, Maturitas, 47:305–14 (2004)). De novo ceramide levels possibly serve as a central effector mechanism in the inflammatory processes central to many diseases and conditions. However, the potential for modulators of SPT to be used as therapeutic agents for diseases and conditions related to ceramide's involvement, as an effector in inflammatory processes, has not previously been shown.

Elevated levels of fatty acids can induce a syndrome that mimics the pathology of cardiomyopathy (i.e., heart failure). The pathogenesis of this lethal condition is poorly understood, but appears to be related to lipotoxicities. Studies indicate that lipid overload in cardiac myocytes may well be an underlying cause for cardiomyopathy. In addition, recent studies have identified low levels of myocyte apoptosis (80–250 myocytes per $10^5$ nuclei) in failing human hearts. It remains unclear, however, whether this cell death is a coincidental finding, a protective process, or a causal component in disease pathogenesis (See, e.g., Wencker D., et al., J. Clin. Invest., 111: 1497–1504 (2003), the disclosure of which is incorporated herein by reference). Increases in fatty acid levels in cells directly lead to elevated rates of de novo ceramide synthesis. TNF has been implicated in CHF, and thereby ceramide, an associated effector for TNF signaling, is implicated through an independent direction (McTieman, C F, et al., Curr Cardiol Rep. 2(3):189–97 (2000)). However, the utility of de novo ceramide synthesis modulators, as agents to block progression of and allow healing of heart muscles in cardiomyopathy, has not been demonstrated.

Cachexia is a progressive wasting syndrome with loss of skeletal muscle mass (Frost R A and Lang C H.; Curr. Opin. Clin. Nutrit. Metab. Care., 255–263 (2005)) and adipose tissue. This syndrome is found in response to infection, inflammation, cancer (Tisdale M J; Langenbecks Arch Surg., 389:299–305 (2004)) or some chronic diseases like rheumatoid arthritis (Rall L C and Roubenoff, R, Rheumatol 43:1219–23 (2004)). Release of various cytokines has been implicated in this syndrome and both TNF and IL-6 are recognized as central players. Thus cachexia can be looked at as a chronic inflammatory state. Ceramide is a well-known central effector of TNF signaling. In addition, ceramide is known to modulate the expression of IL-6 (Shinoda J, Kozawa O, Tokuda H, Uematsu, T. Cell Signal., 11:435–41 (1999)); Coroneos, E; Wang, Y; Panuska, J R; Templeton, D J; Kester, M.; Biochem J; 316:13–7 (1996)). Existing data lead us to believe that de novo ceramide synthesis is playing a central role as a signal for this inflammatory state as well. We therefore believe that inhibition of TNF and /or IL-6 signaling through ceramide will provide a clinical benefit to patients with this wasting syndrome.

Rosenberg and others have shown that isolation of pancreatic islets for transplantation, e.g., for use in the treatment of diabetes, is made difficult by the low yields that result from isolation and that these low yields are due in significant measure to beta cell apoptosis. Structural and functional changes resulting from islet isolation lead to islet cell death (Rosenberg L, Wang R, Paraskevas S, Maysinger D.; Surgery, 126:39398 (1999). Cell loss in isolated human islets occurs by apoptosis. Paraskevas S, Maysinger D, Wang R, Duguid T P, Rosenberg L; Pancreas, 20(3): 270–76 (2000). Challenges facing islet transplantation for the treatment of type 1 diabetes mellitus. Rother K I, Harlan D M, J. Clin. Invest. 114:877–83 (2004)).

Beattie, et al have reported that various treatments (e.g. trehalose, removal of Arg from culture medium, and the like) may improve the yield of transplantable islets but substantial cell death remains (Beattie G M, Leibowitz G, Lopez A D, Levine F, Hayek A, Cell Transplant. 9:431–38) (2000)). Treatment of cells and tissues by caspase inhibitors leads to a partial block of apoptosis in response to various metabolic insults, but apoptosis may be driven by many mechanisms, and caspase inhibition may have useful or marginal effects depending on the specific instance being studied. Study of caspase inhibitors for limiting death in mammalian cell culture. Sauerwald T M, Oyler G A, Betenbaugh M J.) (Biotechnol. Bioeng., 81:329–40 (2003)).

Studies of inhibition of de novo synthesis of ceramide have shown that such inhibition appears to have antiapoptotic effects in a number of important situations. Beta cell apoptosis in response to treatment with free palmitic acid and/or in combination with high levels of glucose can be blocked by treatment with fumonisin B1 (inhibitor of ceramide synthase), for example (Maedler, K. Diabetes, 52:726–33 (2003). It is thus possible that the inhibition or de novo ceramide synthesis can be applied to prevention of apoptotic events. However, treatment with agents that inhibit ceramide synthase have been shown to result in toxic effects, as seen with ingestion of fumonisin B1 (Bennett J W and Klich M., Clin. Microbiol. Rev., 16:497–516 (2003)). Inhibition of SPT provides an alternate method for preventing apoptosis of pancreatic beta cells, however, modulators of SPT have not been shown to prevent the loss of pancreatic beta cells in culture prior to transplant.

Thus, modulators of de novo ceramide synthesis could provide important new therapeutic agents for a range of human and veterinary diseases that entail an inflammatory component making use of ceramide as an effector agent. However, interference with the de novo ceramide synthesis pathway at several points (e.g., as with Fumonisin B1) is known to lead to toxicities. Inhibition at the level of Serine Palmitoyl Transferase, however, leads to the build up of innocuous cellular components serine and Palmitoyl CoA.

Known inhibitors of SPT include cycloserine, D-serine, myriocin, sphingofungin B, viridiofungin A, and lipoxamycin. A number of these natural products, such as myriocin, have been shown to have unacceptable toxicities. Furthermore, these ceramides impart only partially protective activity. In addition, some SPT inhibitors, such as cycloserine, show weak inhibition and exhibit low specificity. Structural studies suggest that natural ceramides mimic the active site bound form of the starting materials or products (Hanada K., et al., Biochem. Biophys. Acta, 1632:16–30 (2003)).

The SPT inhibitor myriocin is known to be a powerful immunosuppressive molecule. A number of analogs have been designed based on its structure. Structures that have the immunosuppressive activity of myriocin, such as those related to compound FTY720, illustrated below, do not inhibit SPT. Additionally, the carboxylic derivative of FTY720, shown below as compound 2, did not exhibit activity against SPT, as demonstrated in an immunosuppressive assay for FTY720-like activity (Kiuchi M. et al., J. Med. Chem., 43:2946–61 (2000)) and was suggested to be inactive due to extremely low solubility if not lack of binding affinity, per se.

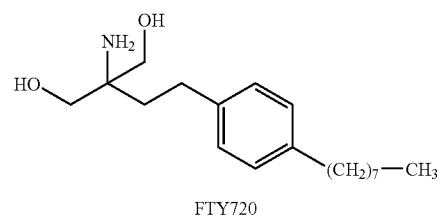

FTY720

-continued

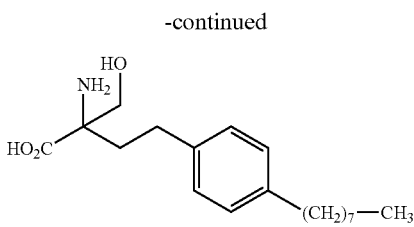

2

Modulation of SPT presents an attractive means to attenuate insulin resistance and prevent loss of pancreatic beta cells. Inhibitors of SPT, in particular, may offer new therapeutics for the treatment of T2D. These agents could be beneficial for the protection of tissue for transplantation such as in islet transplantation and liver transplantation. As outlined above, such inhibitors could also have beneficial uses in the treatment of cardiomyopathy, atherosclerosis, liver damage, reperfusion injury, Alzheimer's Disease, Type 1 diabetes, in which apoptosis plays a role, and other inflammatory diseases. Bio-available agents that are highly potent and selective inhibitors of SPT were, heretofore, not available. Nontoxic, bioavailable, potent and selective modulators of SPT could prove to be important new agents for the treatment of the diseases and conditions as disclosed herein and other diseases and conditions involving apoptosis and in which TNF plays a role as known to those of skill in the art. The generation of such compounds and their usefulness for treating these indications has not been previously shown.

SUMMARY OF THE INVENTION

Presented herein are novel compounds and methods of use. In a preferred embodiment, compounds provided herein exhibit activity on the enzyme, serine palmitoyl transferase (SPT).

Compounds provided herein may be employed in the treatment of a variety of human diseases or conditions. In a preferred embodiment, compounds are used to treat diseases such as T2D, insulin resistance, pancreatic beta cell apoptosis, or obesity. In another preferred embodiment, compounds are used to treat pro-thrombotic conditions, congestive heart failure, myocardial infarction, hypertension, dyslipidemia, or other symptoms of Metabolic Syndrome (i.e., Syndrome X). In yet another preferred embodiment, compounds are used to treat inflammatory diseases, such as inflammatory diseases of the cardiovascular system, sepsis and cachexia. Exemplary inflammatory diseases of the cardiovascular system include atherosclerosis. In yet another preferred embodiment, these compounds are used to prevent liver damage from viral, alcohol related, reperfusion injuries as outlined above. In yet another preferred embodiment, these compounds are used to protect and enhance the yield for transplantation of pancreatic liver cells and or livers, either alone or in combination with the currently approved cocktails and/or caspase inhibitors.

Also provided are compositions comprising compounds presented herein, in combination with a therapeutically effective amount of another active agent. Exemplary agents include insulin, insulin analogs, incretin, incretin analogs, glucagon-like peptide, glucagon-like peptide analogs, exendin, exendin analogs, PACAP and VIP analogs, sulfonylureas, biguanides, α-glucosidase inhibitors, Acetyl-CoA Carboxylase inhibitors, caspase inhibitors, delta 3 unsaturated fatty acids, polyunsaturated fatty acids and PPAR ligands. Accordingly, embodiments of methods for treating various diseases include co-administering compounds presented herein and a therapeutically effective amount of another active agent, or administration of combination compositions provided herein.

DETAILED DESCRIPTION

As used in the specification, "a" or "an" means one or more. As used in the claim(s), when used in conjunction with the word "comprising," the words "a" or "an" mean one or more. As used herein, "another" means at least a second or more.

Reference now will be made in detail to various embodiments and particular applications of the invention. While the invention will be described in conjunction with the various embodiments and applications, it will be understood that such embodiments and applications are not intended to limit the invention. On the contrary, the invention is intended to cover alternatives, modifications and equivalents that may be included within the spirit and scope of the invention. In addition, throughout this disclosure various patents, patent applications, websites and publications are referenced, and unless otherwise indicated, each is incorporated by reference in its entirety for all purposes. All publications mentioned herein are cited for the purpose of describing and disclosing reagents, methodologies and concepts with the present invention. Nothing herein is to be construed as an admission that these references are prior art in relation to the inventions described herein.

I. Compounds

Presented herein are novel compounds, and pharmaceutically acceptable salts thereof, corresponding to Formula (I):

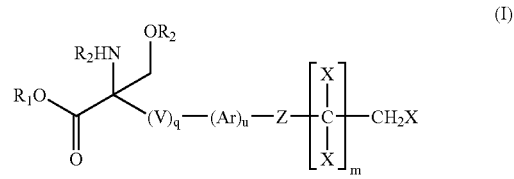

(I)

wherein:
R$_1$ is H or optionally substituted lower alkyl, aryl, aralkyl, or alkyloxyalkyl;
each R$_2$ is independently H, protecting group, or —C(=O)—CHR$_a$—NHR$_b$ where:
R$_a$ is selected from the group consisting of alkyl, aryl, acyl, keto, azido, hydroxyl, hydrazine, cyano, halo, hydrazide, alkenyl, alkynl, ether, thiol, seleno, sulfonyl, borate, boronate, phospho, phosphono, phosphine, heterocyclic, enone, imine, aldehyde, ester, thioacid, hydroxylamine, amino group, and combinations thereof; and
R$_b$ is H or amino protecting group;
each V and Z is independently (CR$_c$R$_d$)$_n$, O, NR$_e$, S, Ar, CR$_c$R$_d$Ar, OAr, NR$_4$Ar, SAr, or
Ar where:
each R$_c$ and R$_d$ is independently H, lower alkyl, OH, O-lower alkyl, or
R$_c$ and R$_d$, taken together, is =O, =N—OH, =N—O-lower alkyl, or =N—O—CH$_2$CH$_2$—O—CH$_3$;
R$_e$ is H, lower alkyl, or —CH$_2$CH$_2$—O—CH$_3$; and
n is 1 to 7;

q is 0 to 3;

Ar is an optionally substituted aryl or heteroaryl;

u is 0 or 1;

each X is independently H or halogen; and m is 4 to 12.

In some embodiments of the invention, compounds of Formula (I) do not include:

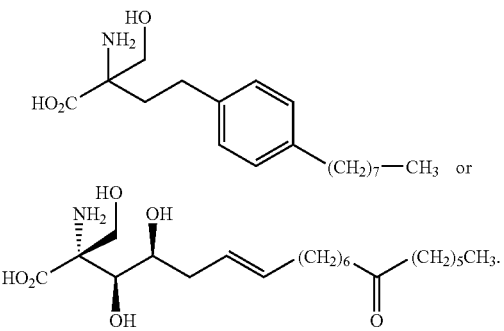 or

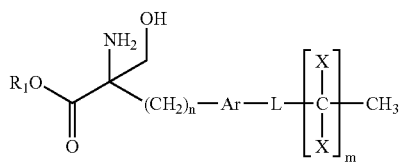

Preferred compounds of Formula (I) include those where $R_1$ is lower alkyl, such as methyl, ethyl, isopropyl, and the like. Additionally preferred embodiments include those compounds where $R_1$ is alkyloxyalkyl, such as $CH_3$—O—$CH_2$—$CH_2$—, HO—$CH_2$—$CH_2$—O—, HO—($CH_2$—$CH_2$—O—)p-, hydroxyethyl alcohol, hydroxypropyl alcohol, hydroxyethyloxyethyl alcohol, and polyethylene glycol or derivatives there. Other preferred compounds of Formula (I) include those where X is halogen, such as fluorine. Additional preferred compounds of Formula (I) include those where Z is $NR_4$, O, or S. Another preferred embodiment includes compounds of Formula (I) where Ar is an optionally substituted heteroaryl. Another preferred embodiment includes compounds of Formula (I) where Ar is an optionally substituted fused ring system, such as a 5-5, 5-6, or 6-6 ring system.

In an embodiment, compounds of Formula (I) correspond to Formula (II):

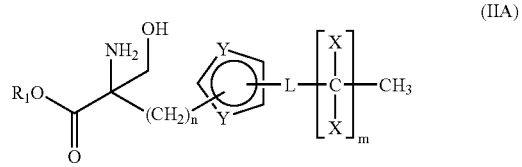

wherein:

L is $CH_2$, $CHR_f$, $CR_fR_g$, O, $NR_h$, S, Ar, $CH_2Ar$, $CHR_fAr$, $CR_fR_gAr$, OAr, $NR_hAr$, SAr, or ArAr, where $R_f$ is H, lower alkyl, OH, O-lower alkyl, $R_g$ is H, or $R_f$ and $R_g$, taken together, is =O, =N—OH, =N—O-lower alkyl, or =N—O—$CH_2CH_2$—O—$CH_3$, and $R_h$ is H, lower alkyl, or —$CH_2CH_2$—O—$CH_3$.

In an embodiment, compounds of Formula (I) correspond to Formula (IIA):

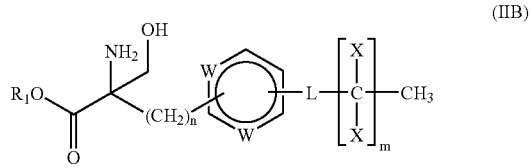

wherein each Y is independently C, CH, O, S, N, or NH.

In another embodiment, compounds of Formula (I) correspond to Formula (IIB):

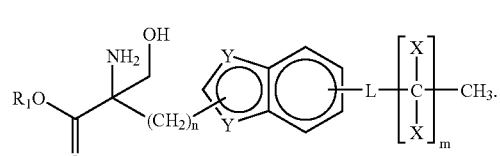

wherein each W is independently C, CH, N, or NH.

In yet another embodiment, compounds of Formula (I) correspond to Formula (IIC):

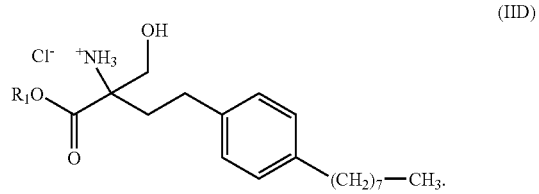

wherein each Y is independently C, CH, O, S, N, or NH.

In another embodiment, compounds of Formula (I) correspond to Formula (IID):

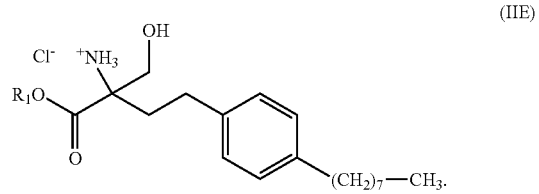

In another embodiment, compounds of Formula (I) correspond to Formula (IIE):

In another embodiment, compounds of Formula (I) correspond to Formula (IIF):

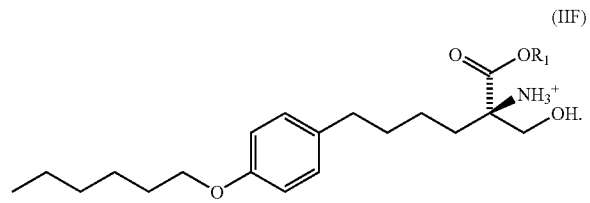
(IIF)

In an additional embodiment, compounds of Formula (I) correspond to Formula (III):

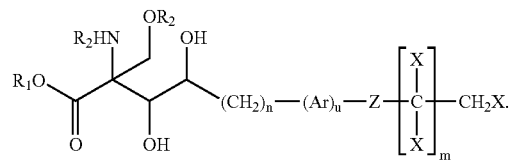
(III)

In another embodiment, compounds of Formula (I) correspond to Formula (IIIA):

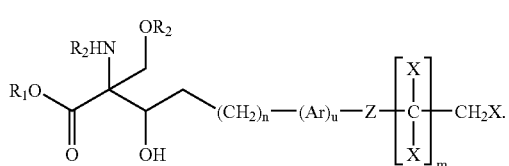
(IIIA)

In another embodiment, compounds of Formula (I) correspond to Formula (IIIB):

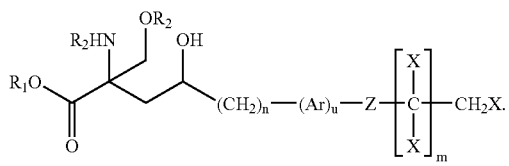
(IIIB)

In another embodiment, compounds of Formula (I) correspond to Formula (IIIC):

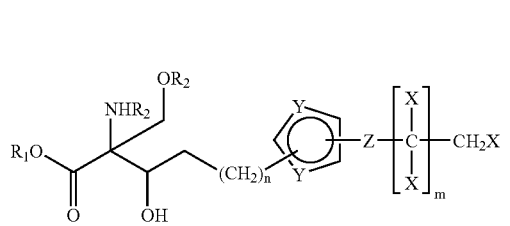
(IIIC)

wherein each Y is independently C, CH, O, S, N, or NH.

In another embodiment, compounds of Formula (I) correspond to Formula (IIID):

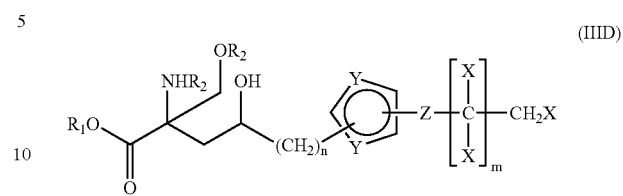
(IIID)

wherein each Y is independently C, CH, O, S, N, or NH.

In another embodiment, compounds of Formula (I) correspond to Formula (IIIE):

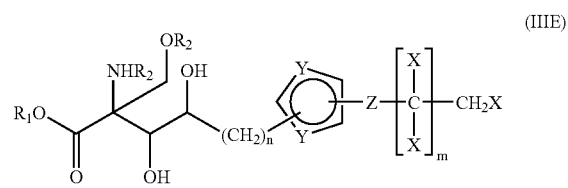
(IIIE)

wherein each Y is independently C, CH, O, S, N, or NH.

In another embodiment, compounds of Formula (I) correspond to Formula (IIIF):

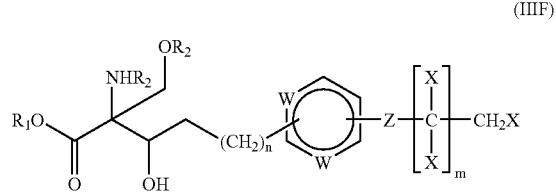
(IIIF)

wherein each W is independently C, CH, N, or NH.

In another embodiment, compounds of Formula (I) correspond to Formula (IIIG):

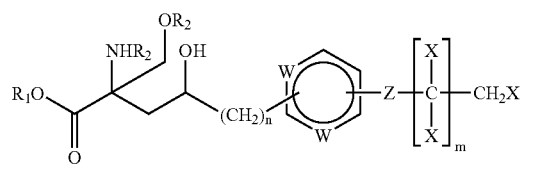
(IIIG)

wherein each W is independently C, CH, N, or NH.

In another embodiment, compounds of Formula (I) correspond to Formula (IIIH):

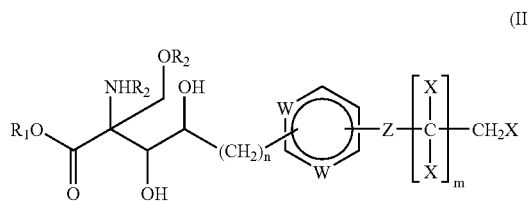

wherein each W is independently C, CH, N, or NH.

In another embodiment, compounds of Formula (I) correspond to Formula (IIIJ):

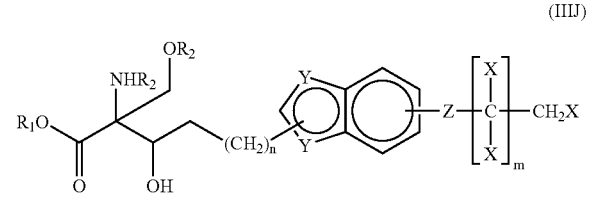

wherein each Y is independently C, CH, O, S, N, or NH.

In another embodiment, compounds of Formula (I) correspond to Formula (IIIK):

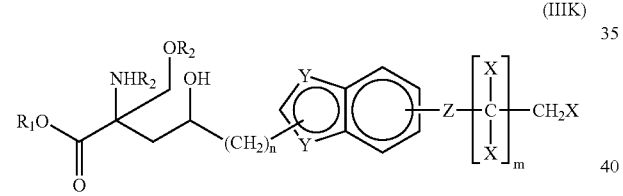

wherein each Y is independently C, CH, O, S, N, or NH.

In another embodiment, compounds of Formula (I) correspond to Formula (IIIL):

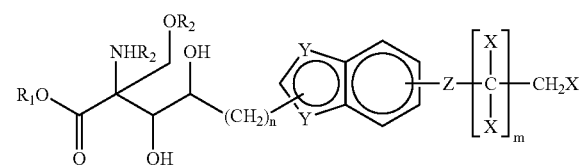

wherein each Y is independently C, CH, O, S, N, or NH.

In yet another embodiment, prodrug forms of compounds of Formula (I) are presented. Prodrug forms of compounds are optimal for oral administration, and typically correspond to the ester of the acid active species. Active species of the prodrugs can be used to prepare active drug compounds.

In an embodiment, prodrug compounds correspond to Formula (IIIM):

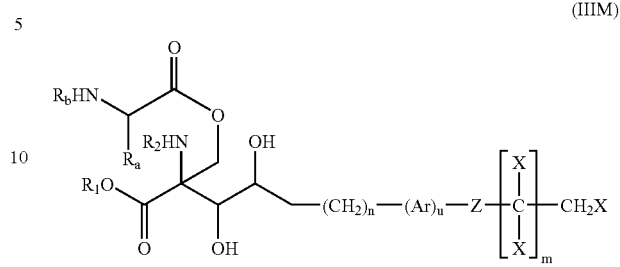

wherein $R_a$ is the side chain of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, pyrolysine and selenocysteine.

Representative prodrug compounds corresponding to Formula (IIIM) include compounds corresponding to Formula (IIIN):

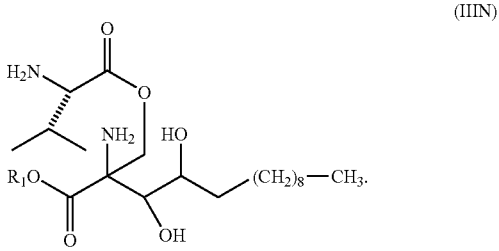

In another embodiment, prodrug compounds correspond to Formula (IIIP):

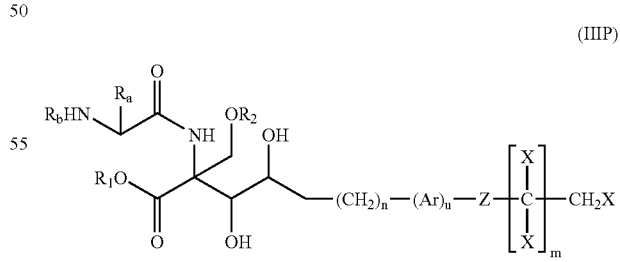

wherein $R_a$ is the side chain of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, pyrolysine and selenocysteine.

Representative prodrug compounds corresponding to Formula (IIIP) include compounds corresponding to Formula (IIIQ):

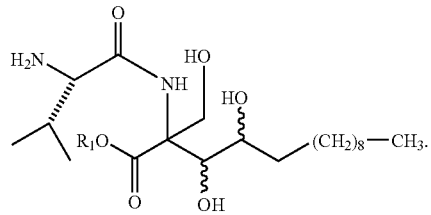

Exemplary chemical structures provided herein are listed below in Table 1. In some embodiments of the invention, representative compounds provided in Table 1 have $R_1$=H, and m=4. In some embodiments of the invention representative compounds provided in Table 1 have $R_1$=$CH_3$, and m=4.

TABLE 1-continued

Representative Chemical Compounds

17–34: (chemical structures)

II. Definitions

Compounds presented herein embrace isotopically-labelled compounds, which are identical to those recited in Formula I, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as $^2$H, $^3$H, $^{13}$C, $^{14}$C, $^{15}$N, $^{18}$O, $^{17}$O, $^{35}$S, $^{18}$F, $^{36}$Cl, respectively. Compounds presented herein, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. $^3$H and $^{14}$C isotopes are preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds herein and prodrugs thereof can generally be prepared by carrying out the procedures disclosed in the Schemes and/or in the Examples below, by substituting a readily available isotopically labelled reagent for a non-isotopically labelled reagent.

Some of the compounds herein have asymmetric carbon atoms and can therefore exist as enantiomers or diastereomers. Diasteromeric mixtures can be separated into their individual diastereomers on the basis of their physical chemical differences by methods known, for example, by chromatography and/or fractional crystallization. Enantiomers can be separated by converting the enantiomeric mixture into a diasteromeric mixture by reaction with an appropriate optically active compound (e.g., alcohol), separating the diastereomers and converting (e.g., hydrolyzing) the individual diastereomers to the corresponding pure enantiomers. Enantiomers can also be synthesized using asymmetric reagents, for example to prepare the alpha alkyl amino acid head group of myriocin and its analogs (e.g., Seebach, D., et al. Helv. Chim. Acta., 70:1194–1216 (1987)); Hale, J J, et al. Bio-org. Med. Chem. Lett., 12:4803–07 (2004)); Kobayashi, S., et al., J. Am. Chem. Soc., 120:908–19 (1998)). Alternatively, chiral synthesis of enantiomeric centers using chiral synthons from natural products is a facile approach to such syntheses, for example the synthesis of myriocin from d-mannose (Oishi, T., et al. Chemical Commun. 1932–33 (2001)); and references to myriocin synthesis therein) and of myriocin analogs from isolated, natural myriocin (Chen, J K, et al. Chem Biol. 6, 221–35 (1999)); Fujita, T, et al. J. Med. Chem. 39, 4451–59 (1996)). In addition, use of enzymes (free or supported) to preferentially modify one of the enantiomeric centers and thus allow separation or interconversion of enantiomers is well-known to the art (for example Wang, Y. -F., et al. (1988). J. Am. Chem. Soc. 110, 7200–5) and has great usefulness in production of pharmaceuticals. All such isomers, including diastereomers, enantiomers, and mixtures thereof are considered as part of this invention.

Those skilled in the art will recognize that some of the compounds herein can exist in several tautomeric forms. All such tautomeric forms are considered as part of this invention. Also, for example all enol-keto forms of any compounds herein are included in this invention.

Some of the compounds of this invention are acidic and may form a salt with a pharmaceutically acceptable cation. Some of the compounds of this invention can be basic and accordingly, may form a salt with a pharmaceutically acceptable anion. All such salts, including di-salts are within the scope of this invention and they can be prepared by conventional methods. For example, salts can be prepared simply by contacting the acidic and basic entities, in either an aqueous, non-aqueous or partially aqueous medium. The salts are recovered either by filtration, by precipitation with a non-solvent followed by filtration, by evaporation of the solvent, or, in the case of aqueous solutions, by lyophilization, as appropriate.

In addition, compounds herein embrace metabolites, hydrates, or solvates thereof and all of which are within the scope of the invention.

The term "substituted" refers to substitution on any carbon or heteroatom with any chemically feasible substituent. Representative substitutions include halogen substitution or substitution with any heteroatom containing group, e.g., alkoxy, phophoryl, sulfhydryl, etc.

The term "alkyl" refers to straight chain, branched, or cyclic hydrocarbons. Exemplary of such alkyl groups (assuming the designated length encompasses the particular example) are methyl, ethyl, propyl, isopropyl, butyl, sec-butyl, tertiary butyl, pentyl, isopentyl, neopentyl, tertiary pentyl, 1-methylbutyl, 2-methylbutyl, 3-methylbutyl, hexyl, isohexyl, heptyl and octyl. The term "lower alkyl" refers to alkyl as defined above comprising $C_1$–$C_{20}$. Substituted alkyl refers to alkyl groups which are substituted as defined above and are exemplified by haloalkyl, e.g., $CF_3$, $CHF_2$, $CH_2F$, etc.

The term "aryl" refers to any aromatic group comprising $C_3$–$C_{20}$. Aryl groups also embrace fused ring systems, such as 5-5, 5-6, and 6-6 ring systems. Representative aryl groups include phenyl, biphenyl, anthracyl, norbomyl, and the like. Aryl groups may be substituted according to the definition provided above.

The term "heteroaryl" refers to any aryl group comprising at least one heteroatom within the aromatic ring. Heteroaryl groups also embrace fused ring systems, such as 5-5, 5-6, and 6-6 ring systems. Representative heteroaryl groups include imidazole, thiazole, oxazole, phenyl, pyridinyl, pyrimidyl, imidazolyl, benzimidazolyl, thiazolyl, oxazolyl, isoxazolyl, benzthiazolyl, or benzoxazolyl. Heteroaryl groups may be substituted according to the definition provided above.

The term "aralkyl" or "arylalkyl" refers to an aryl group comprising an alkyl group as defined above. Aralkyl or arylalkyl groups may be appended from the aryl or the alkyl moiety.

The term "alkoxy" refers to alkyl groups bonded through an oxygen. Exemplary alkoxy groups (assuming the designated length encompasses the particular example) are methoxy, ethoxy, propoxy, isopropoxy, butoxy, isobutoxy, tertiary butoxy, pentoxy, isopentoxy, neopentoxy, tertiary pentoxy, hexoxy, isohexoxy, heptoxy and octoxy. Alkoxy may be substituted according to the definition provided above.

The term "alkoxyalkyl" refers to an alkoxy group comprising an alkyl group as defined above. Alkoxyalkyl groups may be substituted according to the definition provided above.

The term "halogen" refers to chloro, bromo, iodo, or fluoro.

The term "modulator" means a molecule that interacts with a target either directly or indirectly. The interactions include, but are not limited to, agonist, antagonist, and the like.

The term "agonist" means a molecule such as a compound, a drug, an enzyme activator or a hormone that enhances the activity of another molecule or the activity of a receptor site.

The term "antagonist" means a molecule such as a compound, a drug, an enzyme inhibitor, or a hormone, that diminishes or prevents the action of another molecule or the activity of a receptor site.

The terms "effective amount" or "therapeutically effective amount" refer to a sufficient amount of the agent to provide the desired biological result. That result can be reduction and/or alleviation of the signs, symptoms, or causes of a disease, or any other desired alteration of a biological system. For example, an "effective amount" for therapeutic use is the amount of the composition comprising a compound as disclosed herein required to provide a clinically significant decrease in a disease. An appropriate "effective" amount in any individual case may be determined by one of ordinary skill in the art using routine experimentation.

As used herein, the terms "treat" or "treatment" are used interchangeably and are meant to indicate a postponement of development of diseases and/or a reduction in the severity of such symptoms that will or are expected to develop. The terms further include ameliorating existing disease symptoms, preventing additional symptoms, and ameliorating or preventing the underlying metabolic causes of symptoms.

By "pharmaceutically acceptable" or "pharmacologically acceptable" is meant a material which is not biologically or otherwise undesirable, i.e., the material may be administered to an individual without causing any undesirable biological effects or interacting in a deleterious manner with any of the components of the composition in which it is contained.

III. Preparation of Compounds

Compounds provided herein can be prepared by synthetic methods well known to those skilled in the art. Exemplary references discussing representative preparative methods which maybe employed include: Kiuchi, et al., J. Med. Chem., 43:2946–61 (2000); Seidel G., et al., J. Org. Chem., 69:3950–52 (2004); Clemens J. J., et al., Bioorg. Med. Chem. Lett., 14:4903–06 (2004); Durand, P., et al., Synthesis, 505:6 (2000); Hale et al., Bioorg. Med. Chem. Lett., 14:3351–55 (2004); Seebach, D., et al., Helv. Chim. Acta., 70:1194–1216 (1987)); Oishi, T, et al. (2001), Chem. Commun. 1932–3; Wang, Y. -F., et al., J. Am. Chem. Soc. 110, 7200–05 (1988)); Pipik, B, et al., Synth. Commun. 34, 1863–70 (2004)); the disclosures of all of which are incorporated herein by reference.

General methods of synthesis, especially synthesis of esters are provided in "Comprehensive Organic Transformations" $2^{nd}$ Edition, Larock, R C, Wiley, N.Y., 1999 and "Protective Groups in Organic Synthesis", Greene T and Wuts P G M, Edition 3, Wiley, N.Y., 1999.

Kiuchi et al. (Kiuchi M, et al., J. Med. Chem., 43:2946–61 (2000)) discusses procedures for the synthesis of compound 2. Representative methods for preparing compounds herein may include synthetic precursors reported therein. The general sequence (Scheme 1) for preparing Cα-substituted serine moieties from alkyl halides (or from the corresponding hydroxyl or aldehyde structures by conversion to alkyl halides) can be used broadly to prepare the present compounds. Illustrated in the synthetic schemes below are exemplary methods for preparing the present compounds.

Scheme 1 below illustrates a preparative route reported in Kiuchi et al. for preparing compound 2.

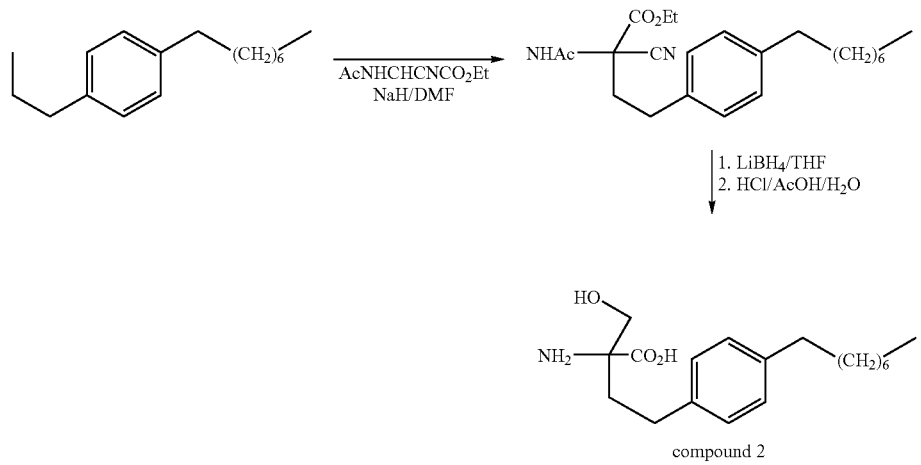

compound 2

Scheme 2 illustrates a similar synthetic procedure for preparing of an analog having increased water solubility.

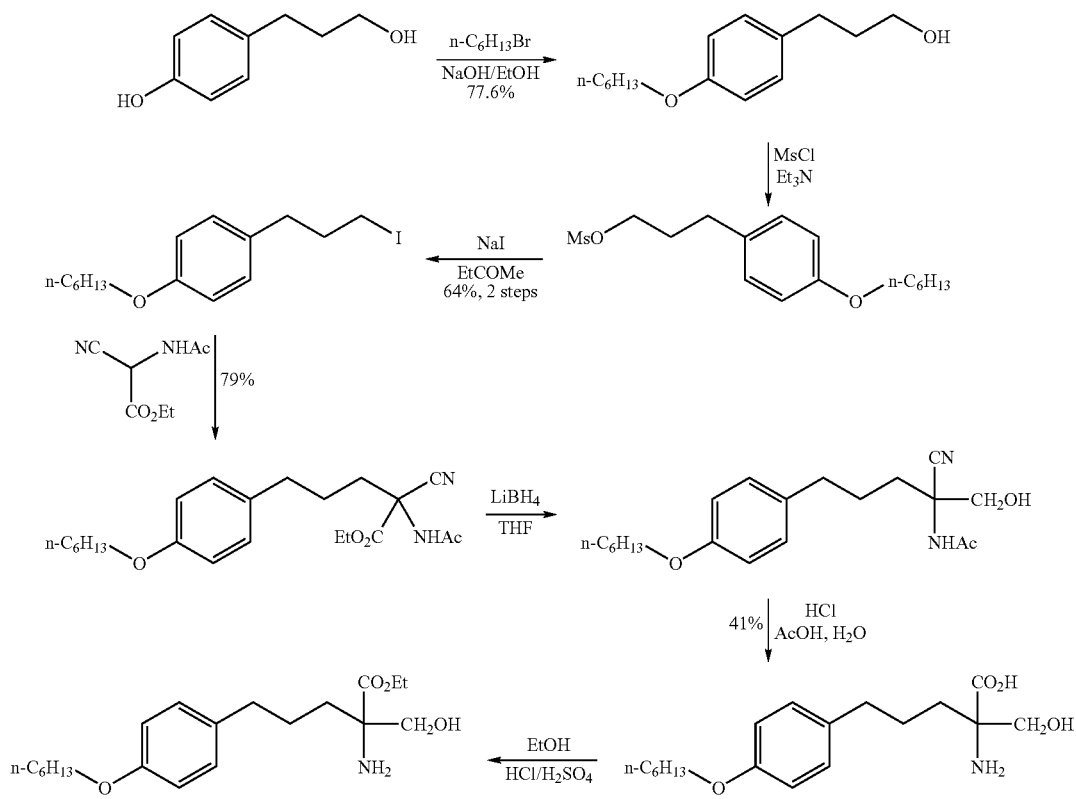

As illustrated in Scheme 3 below, analogs of myriocin which contain two hydroxyl functional groups alpha and beta to the head group, can be prepared from native myriocin using a variation of the approach reported by Chen, JK, et al. (1999). Shown below is an exemplary synthetic procedure using starting material reported in Chen et al. to obtain a range of analogs having various functionalities in R' by employing a Wittig-type reaction with iodoalkyl compounds. For example, R' can be alkyl, haloalkyl, aryl, aralkyl, and the like. Scheme 3 is a chiral preparation and corresponding enantiomers can be produced using this procedure by protecting the primary OH and NH/CO$_2$H functional groups, followed by inversion chemistry on the secondary OH groups. Exemplary compounds 13, 17, and 18 are readily prepared from the corresponding jodoalkyl compounds using the procedure illustrated below.

Compounds having a single hydroxyl function alpha to the serine head group can be prepared in the synthetic method illustrated below in Scheme 4. Similar reagents may be used to carry out these synthetic steps with greater or lesser yields, depending on the actual substrates used. Exemplary compounds 14, 19, and 21 are readily prepared using Scheme 4.

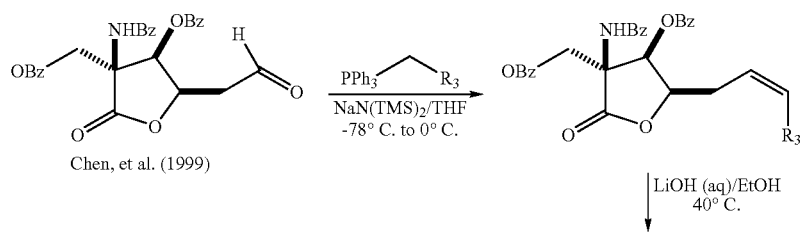

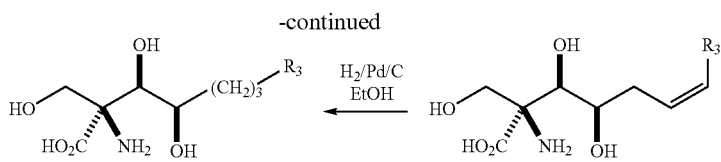

Compounds having a single hydroxyl function alpha to the serine head group can be prepared in the synthetic method illustrated below in Scheme 4. Similar reagents may be used to carry out these synthetic steps with greater or lesser yields, depending on the actual substrates used. Exemplary compounds 14, 19, and 20 are readily prepared using Scheme 4.

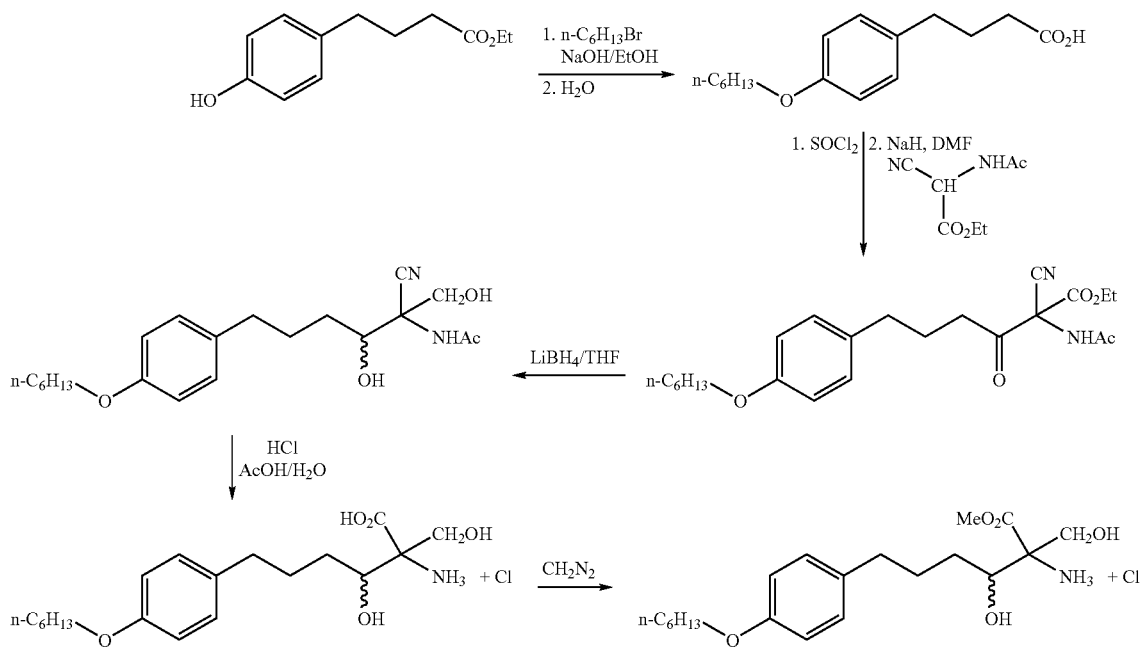

Similarly, compounds with a single hydroxyl function, beta to the serine like head group (e.g. compound 20) are prepared through a route starting from the corresponding, readily available alpha-haloketones or alpha-hydroxyketones according to Scheme 5.

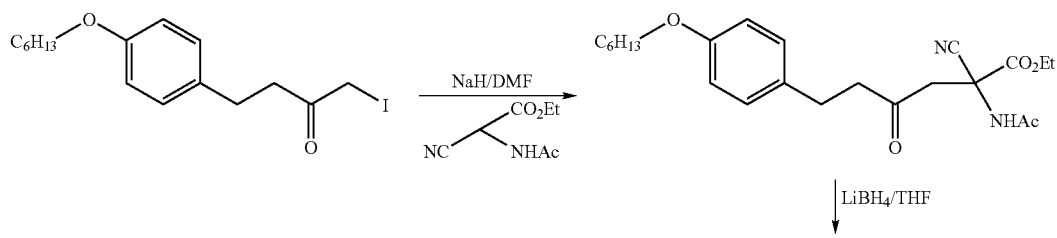

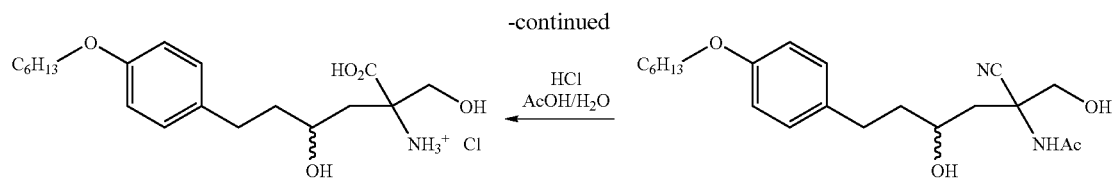

IV. Pharmaceutical Compositions

Compositions presented herein include compounds provided herein and a pharmaceutically acceptable carrier.

A. Formulations

Pharmaceutically useful compositions comprising the compounds of the present invention may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the compound, e.g., a prodrug or an active species (e.g., the corresponding acid of the ester or prodrug), of the present invention.

Suitable formulations for administering the present compounds include topical, transdermal, oral, systemic, and parenteral pharmaceutical formulations. Compositions containing compounds herein can be administered in a wide variety of therapeutic dosage forms in conventional vehicles for administration. For example, the compounds or modulators can be administered in such oral dosage forms as tablets, capsules (each including timed release and sustained release formulations), pills, powders, granules, elixirs, tinctures, solutions, suspensions, syrups and emulsions, or by transdermal delivery or injection. Likewise, they may also be administered in intravenous (both bolus and infusion), intraperitoneal, subcutaneous, topical with or without occlusion, transdermal, or intramuscular form, all using forms well known to those of ordinary skill in the pharmaceutical arts. The present compounds may be delivered by a wide variety of mechanisms, including but not limited to, transdermal delivery, or injection by needle or needle-less injection means.

B. Dosages

Embodiments include pharmaceutical compositions comprising an effective amount of compounds presented herein. Effective dosages of compounds disclosed herein may be defined by routine testing in order to obtain optimal inhibition of serine palmitoyl transferase while minimizing any potential toxicity.

As is well known to one of skill in the art, effective amounts can be routinely determined and vary according to a variety of factors such as the individual's condition, weight, sex, age, medical condition of the patient, severity of the condition to be treated, route of administration, renal and hepatic function of the patient, and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

An effective but non-toxic amount of the compound desired can be employed as a serine palmitoyl transferase-modulating agent. Dosages contemplated for administration of the present compounds range from 0.01 to 1,000 mg per patient, per day. For oral administration, the compositions are preferably provided in the form of scored or un-scored tablets containing 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. Dosage amounts may also vary by body weight and can range, for example, from about 0.0001 mg/kg to about 100 mg/kg of body weight per day, preferably from about 0.001 mg/kg to 10 mg/kg of body weight per day.

Compounds may be administered in a single daily dose, or the total daily dosage may be administered in divided doses of two, three, or four times daily. To be administered in the form of a transdermal delivery system, the dosage administration will be continuous rather than intermittent throughout the dosage regimen.

The dosages of the compounds of the present invention are adjusted when combined with other therapeutic agents. Dosages of these various agents may be independently optimized and combined to achieve a synergistic result wherein the pathology is reduced more than it would be if either agent were used alone. In addition, co-administration or sequential administration of other agents may be desirable.

C. Derivatives

Embodiments of compounds presented herein include "chemical derivatives." Chemical derivatives comprise compounds herein and additional moieties that improve the solubility, half-life, absorption, etc. of the compound. Chemical derivatives may also comprise moieties that attenuate undesirable side effects or decrease toxicity. Examples of such moieties are described in a variety of texts, such as Remington's Pharmaceutical Sciences, and are well known to one of skill in the art.

D. Carriers and Excipients

Compounds herein can be administered in admixture with suitable pharmaceutical diluents, excipients, or carriers (collectively referred to herein as "carrier" materials) suitably selected with respect to the intended form of administration, that is, oral tablets, capsules, elixirs, syrups and the like, and consistent with conventional pharmaceutical practices.

For oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For liquid forms the active drug component can be combined in suitably flavored suspending or dispersing agents such as the synthetic and natural gums, for example, tragacanth, acacia, methyl-cellulose and the like. Other dispersing agents which may be employed include glycerin and the like.

For parenteral administration, sterile suspensions and solutions are desired. Isotonic preparations which generally contain suitable preservatives are employed when intravenous administration is desired.

Topical preparations comprising the present compounds can be admixed with a variety of carrier materials well known in the art, such as alcohols, aloe vera gel, allantoin, glycerine, vitamin A and E oils, mineral oil, PPG2 myristyl propionate, and the like, to form, for example, alcoholic solutions, topical cleansers, cleansing creams, skin gels, skin lotions, and shampoos in cream or gel formulations.

Compounds can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidyicholines.

Compounds presented herein may also be delivered by the use of monoclonal antibodies as individual carriers to which the compound molecules are coupled. Compounds may be coupled with soluble polymers as targetable drug carriers. Such polymers can include polyvinyl-pyrrolidone, pyran copolymer, polyhydroxypropylmethacryl-amidephenol, polyhydroxy-ethylaspartamideplhenol, or polyethyl-eneoxidepolylysine substituted with palmitoyl residues. Furthermore, compounds may be coupled to biodegradable polymers useful in achieving controlled release of a drug, such as polylactic acid, polyepsilon caprolactone, polyhydroxy butyric acid, polyorthoesters, polyacetals, polydihydro-pyrans, polycyanoacrylates, cross-linked or amphipathic block copolymers of hydrogels, and other suitable polymers known to those skilled in the art.

For oral administration, compounds may be administered in capsule, tablet, or bolus form. The capsules, tablets, and boluses comprise an appropriate carrier vehicle, such as starch, talc, magnesium stearate, or di-calcium phosphate.

Unit dosage forms are prepared by intimately mixing compounds with suitable finely-powdered inert ingredients including diluents, fillers, disintegrating agents, and/or binders such that a uniform mixture is obtained. An inert ingredient is one that will not adversely react with the compounds. Suitable inert ingredients include starch, lactose, talc, magnesium stearate, vegetable gums and oils, and the like. Compounds can be intimately mixed with inert carriers by grinding, stirring, milling, or tumbling.

Injectable formulations comprise compounds herein mixed with an appropriate inert liquid carrier. Acceptable liquid carriers include the vegetable oils such as peanut oil, cottonseed oil, sesame oil and the like as well as organic solvents such as solketal, glycerol formal and the like. As an alternative, aqueous parenteral formulations may also be used. The vegetable oils are the preferred liquid carriers. The formulations are prepared by dissolving or suspending the compound in a liquid carrier.

Topical application of compounds is possible through the use of, for example, a liquid drench or a shampoo containing the instant compounds or in modulators as an aqueous solution or suspension. These formulations may comprise a suspending agent such as bentonite and optionally, an anti-foaming agent.

E. Modes of Administration

Other factors affecting dosage amounts are the modes of administration. The pharmaceutical compositions of the present invention may be provided to the individual by a variety of routes including, but not limited to subcutaneous, intramuscular, intra-venous, topical, transdermal, oral and any other parenteral or non-parenteral route. Furthermore, compounds can be administered in intranasal form via topical use of suitable intranasal vehicles, or via transdermal routes, using those forms of transdermal skin patches well known to those of ordinary skill in that art.

The compounds or modulators may alternatively be administered parenterally via injection of a formulation consisting of the active ingredient dissolved in an inert liquid carrier. Injection may be either intramuscular, intraruminal, intratracheal, or subcutaneous, either by needle or needle-less means.

F. Pharmaceutically Acceptable Salts

Embodiments include compounds presented herein in the form of a free base or as a pharmaceutically acceptable salt. Exemplary pharmaceutically acceptable salts include hydrobromic, hydroiodic, hydrochloric, perchloric, sulfuric, maleic, fumaric, malic, tartaric, citric, benzoic, mandelic, methanesulfonic, hydroethanesulfonic, benzenesulfonic, oxalic, pamoic, 2-naphthalenesulfonic, p-toluenesulfonic, cyclohexanesulfamic and saccharic. Ion exchange, metathesis or neutralization steps may be used to form the desired salt form.

G. Combinations

Embodiments include compositions comprising compounds presented herein in combination with another active agent. Exemplary active agents which may be employed include insulin, insulin analogs, incretin, incretin analogs, glucagon-like peptide, glucagon-like peptide analogs, exendin, exendin analogs, PACAP and VIP analogs, sulfonylureas, biguanides, α-glucosidase inhibitors, and ligands for the Peroxisome Proliferator-Activated Receptors (PPARs) of all classes.

For combination treatment with more than one active agent, where the active agents are in separate dosage formulations, the active agents can be administered concurrently, or they each can be administered at separately staggered times.

The dosages of the compounds of the present invention are adjusted when combined with other therapeutic agents. Dosages of these various agents may be independently optimized and combined to achieve a synergistic result wherein the pathology is reduced more than it would be if either agent were used alone. In addition, co-administration or sequential administration of other agents may be desirable H. Kits In a preferred embodiment, compounds herein are packaged in a kit. An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc . . . Second Week, Monday, Tuesday, . . ." etc. Other variations of memory aids will be readily apparent. A "daily dose" can be a single tablet or capsule or several pills or capsules to be taken on a given day. Also, a daily dose of Formula I compound can consist of one tablet or capsule while a daily dose of the second compound can consist of several tablets or capsules and vice versa. The memory aid should reflect this.

In another specific embodiment of the invention, a dispenser designed to dispense the daily doses one at a time in the order of their intended use is provided. Preferably, the dispenser is equipped with a memory aid, so as to further facilitate compliance with the regimen. An example of such a memory aid is a mechanical counter which indicates the number of daily doses that has been dispensed. Another example of such a memory aid is a battery powered microchip memory coupled with a liquid crystal readout, or audible reminder signal which, for example, reads out the date that the last daily dose has been taken and/or reminds one when the next dose is to be taken.

V. Methods of Treatment

An important feature of the present invention relates to the involvement of ceramide as a signaling molecule in inflammatory processes. In addition to its effect on the apoptosis of beta cells relevant to T2D, de novo ceramide can have broader apoptotic effects in human health. Influencing the levels of ceramide can lead to novel treatments of human islets, or islets from other commercially or medicinally important sources, in culture during isolation for transplant with the intent of improving survival of islets in vitro and post transplant. SPT inhibitors can be added to currently used or accepted treatment protocols in order to inhibit, either alone and/or in a synergistic fashion, the loss of islets and beta cells due to apoptotic and/or necrotic processes.

Such basic protocols to be improved on are described in Beattie, et al. 2000 (above, and references therein) and in publications describing the "Edmonton Protocol" (Diabetes. 2001;50:710–9. Clinical outcomes and insulin secretion after islet transplantation with the Edmonton protocol. Ryan E A, Lakey J R, Rajotte R V, Korbutt G S, Kin T, Imes S, Rabinovitch A, Elliott J F, Bigam D, Kneteman N M, Warnock G L, Larsen I, Shapiro A M, and references therein). These protocols may involve the addition of trehalose cryoprotectant and removal of Arg (Diabetes. 46:519–23 (1997). Trehalose: a cryoprotectant that enhances recovery and preserves function of human pancreatic islets after long-term storage. Beattie G M, Crowe J H, Lopez A D, Cirulli V, Ricordi C, Hayek A.), fetal bovine serum, transferrin, selenium (Cell Tissue Bank., 4(2/4):85–93 (2003). A comparative evaluation of culture conditions for short-term maintenance (<24 hr) of human islets isolated using the Edmonton protocol. Matsumoto S, Goel S, Qualley S, Strong D M, Reems J A.), or various caspase inhibitors such as Z-VAD-FMK and B-D-FMK (Biotechnol. Bioeng., 81(3):329–40 (2003). Study of caspase inhibitors for limiting death in mammalian cell culture. Sauerwald T. M., Oyler G. A., Betenbaugh M. J.; Nephron. Exp. Nephrol., 96(2):e39–51 (2004). Inhibitors directed towards caspase-1 and -3 are less effective than pan caspase inhibition in preventing renal proximal tubular cell apoptosis. Yang B, El Nahas A M, Fisher M, Wagner B, Huang L, Storie I, Barnett D, Barratt J, Smith A C, Johnson T S.), nicotinamide, sodium butryrate (Transplantation., 68(11):1674–83 (1999)). Differentiation and maturation of porcine fetal islet cells in vitro and after transplantation. Otonkoski T, Ustinov J, Rasilainen S, Kallio E, Korsgren O, Hayry P.), caerulein, IBMX (Pancreas. 6:625–30 (1991)). Survival and B-cell function of neonatal pig pancreatic islet-like cell clusters in an extracellular matrix. Ohgawara H, Mochizuki N, Karibe S, Omori Y.), IGF-II (J Endocrinol. 161:357–64 (1999)). Pancreatic islet cell survival following islet isolation: the role of cellular interactions in the pancreas. Ilieva A, Yuan S, Wang R N, Agapitos D, Hill D J, Rosenberg L.), and the like.

Blockade of de novo ceramide synthesis shows a synergistic improvement in cell survival when comprising addition of compounds of the present invention, e.g., SPT inhibitors, to the protocols enumerated above, and their like. Loss of pancreatic islets in Type 1 Diabetes also shows evidence of inflammatory processes leading to apoptosis and necrosis.

Embodiments of the invention include methods for treating developing Type 1 Diabetes and/or the further loss of islets following transplantation (human or xenobiotic islet cell transplantation) comprising the addition of compounds of the present invention, e.g., SPT inhibitors, to current treatment protocols (IUBMB Life. 2004 July, 56:387–94. Protecting pancreatic beta-cells. Pileggi A, Fenjves E S, Klein D, Ricordi C, Pastori R L.). Xenobiotic cells contemplated for use in the methods of the present invention include, but are not limited to, porcine, bovine, murine, and other mammalian cell types. The inhibition of de novo ceramide synthesis shows beneficial effects when used alone or as an addition to existing protocols. Such treatment may commence immediately upon detection of loss of beta cell mass or function, and be used alone or in conjunction with immunosuppressive regimens (cyclosporine, mycophenolic acid agents, FTY720, and the like, for example). This is a broadly based mechanism to protect beta cells from a wide array of insults that result in apoptosis and necrosis.

In additional embodiments of this invention, the compounds of the invention are used for the blockade of apoptosis of neuronal cells following spinal injury, and in loss of CNS neurons, e.g. in Alzheimer's disease or stroke. This treatment with an inhibitor of SPT may be used effectively alone or in combination with other treatments such as antioxidants, caspase inhibitors (Neurochem Res., 28:143–52 (2003). Protection of mature oligodendrocytes by inhibitors of caspases and calpains. Benjamins J A, Nedelkoska L, George E B) and/or other treatments for protection from the late effects of stroke that are well known to those skilled in the art.

Compounds and compositions presented herein may be administered to patients in the treatment of a variety of diseases. Preferably, methods of treatment presented herein are directed to patients (i.e., humans and other mammals) with disorders or conditions associated with the activity or hyperactivity of serine palmitoyl transferase (SPT). Accordingly, methods of treating insulin resistance and cardiomyopathy are provided. Compounds effective in treating cardiomyopathy may interfere with the process of cardiomyopathy development. Compounds of the invention may also be used to treat cachexia and sepsis.

Preferred compounds employed in methods of treatment possess desirable bio-availability characteristics. Exemplary compounds are esters which can function as a pro-drug form having improved solubility, duration of action, and in vivo potency. Preferred compounds employed in treatment methods exhibit improved solubility in water and less potential to cross the blood brain barrier to cause side effects, such as altered feeding behavior.

Pharmaceutical compositions are administered to an individual in amounts sufficient to treat or diagnose disorders in which modulation of serine palmitoyl transferase activity is indicated. Examples of diseases or conditions known to be, or suspected of being mediated by serine palmitoyl transferase include, but are not limited to, insulin resistance, type 2 diabetes and its complications, obesity, pro thrombotic conditions, myocardial infarction, congestive heart failure, hypertension, dyslipidemia, and other manifestations of the commonly accepted "Metabolic Syndrome" and "Syndrome X." Compounds effective in treatment methods herein potently and specifically modulate the enzyme Serine Palmitoyl Transferase.

It is to be understood that the above description is intended to be illustrative and not restrictive. The scope of the invention should, therefore, be determined not with reference to the above description, but instead with reference to the appended claims along with the full scope of equivalents thereto.

EXAMPLES

In order to illustrate the invention the following examples are included. These examples do not limit the invention. They are meant to illustrate only exemplary methods and compounds presented herein. Those knowledgeable in chemical synthesis and the treatment of serine palmitoyl transferase related disorders may find other methods of practicing the invention. However those methods are deemed to be within the scope of this invention.

Example 1

Synthesis of Methyl Ester of Compound 2

In a round-bottomed flask, 500 mL of MeOH is cooled to −5° C. and treated with 0.11 mol of $SOCl_2$ in a dropwise fashion with stirring. Powdered compound 2 (0.1 mol) is added immediately with cooling and stirring. The solution is allowed to warm slowly to room temperature over a period of 2 hrs. Evaporation of the excess MeOH provides the desired compound ($R_1$=Me) as the HCl salt in high yield as a white powder. Recrystallization from a suitable solvent (MeOH/$Et_2O$) provides the desired compound in high purity as a white, waxy solid. In a like manner, additional ester forms of compound herein can be prepared. Synthesis of compound 2 is described in Kiuchi et al. 2000 (supra).

Example 2

Synthesis of Ethyl Ester of Compound 2

In a round-bottomed flask, 500 mL of EtOH is treated with 0.01 mol of HCl in EtOAc and powdered compound 2 (0.1 mol) is added immediately with cooling and stirring. The solution is warmed to reflux and heated for a period of 24 hrs. Evaporation of the excess EtOH provides the desired compound ($R_1$=Me) as the HCl salt in high yield as a white powder. Recrystallization from a suitable solvent (EtOH/$Et_2O$) provides the desired compound in high purity as a colorless oil which slowly forms a waxy solid. In a like manner, additional ester forms of compound herein can be prepared. Alternatively, addition of an equivalent amount of HCl and H2SO4 in EtOH and refluxing for 2 days provides a high yield of product.

Example 3

Synthesis of Compound 23

Compound 23 was prepared using the route outlined in Scheme 2, starting with 4-(3-hydroxypropyl)phenol (Aldrich Chemical Company). Yields obtained are reported in Scheme 2. Compound 23 was obtained as an off white solid and melting point was broad.

(M−1) molecular ion is 322.3 a.m.u. $^1$H NMR ($CD_3OD$) δ: 0.95 (3H, tr), 1.37 (4H, m), 1.45 (2H, m), 1.75 (6H, m), 2.55 (2H, m), 3.7 (2H, dd), 3.9 (2H, t), 6.9 (4H, dd).

Example 4

Synthesis of Compound 24

Compound 24 was prepared using the route outlined in Scheme 2 starting with 4-(4-hydroxybutyl)phenol. Compound 24 was obtained as an off white solid and melting point was broad.

(M−1) molecular ion is 336.3 a.m.u. $^1$H NMR ($D_6$-DMSO) δ: 0.93 (3H, t), 1.4 (12H, broad m), 2.45 (2H, d), 3.5 (2H, q), 3.9 (2H, t), 6.9 (4H, dd).

Example 5

Beta Cell Apoptosis Assay

Rat Pancreatic Islets.

Biological assays are performed as according to Shimabukuro et al., J. Biol. Chem., 273:32487–90 (1998)) with certain modifications. Zucker Diabetic Fatty rats are treated for 2 weeks by i.p. injection with compounds presented herein. Pancreatic islets are isolated and the degree of apoptosis is evaluated by electrophoresis. A significant degree of protection is noted for the treated rats in comparison to the control rats. This protection demonstrates that de novo synthesis of ceramide through the SPT pathway is inhibited specifically and results in protection of beta cells from apoptosis.

Human Pancreatic Islets.

An alternative assay for the detection of beta cell apoptosis is performed according to Maedler, K, et al. (2003). Diabetes 52, 726–33). In this assay, incubation with elevated palmitic acid or elevated glucose causes increased apoptosis and protective effects of inhibitors of ceramide synthase exhibit beneficial effects. Results from this assay demonstrate the beneficial effects of the present compounds to inhibit de novo ceramide synthesis at a different, earlier point in the enzymatic pathway, such as inhibition of SPT.

Islet Isolation and Culture

Islets are isolated from pancreata of organ donors, as described in Oberholzer J. et al. Transplantation 69:1115–23

(2000)). The islet purity is >95% which is determined by dithizone staining. When this degree of purity is not primarily achieved by routine isolation, islets are handpicked. The donors are typically heart-beating cadaver organ donors without a previous history of diabetes or metabolic disorders.

As reported by Maedler et al. (2003), for long-term in vitro studies, the islets are cultured on extracellular matrix-coated plates derived from bovine corneal endothelial cells (Novamed, Jerusalem, Israel), and the cells are allowed to attach to the dishes and spread, to preserve their functional integrity. The contamination by ductal cells after 4 days in culture is estimated to be between 5 and 15%, but almost all ductal cells are found in the periphery of the islets and do not co-localize with β-cells. Islets are cultured in CMRL 1066 medium containing 100 units/ml penicillin, 100 µg/ml streptomycin, and 10% FCS (Gibco, Gaithersburg, Md.), hereafter referred to as culture medium.

Two days after plating, when most islets are attached and begin to flatten, the medium is changed to culture medium containing 5.5 or 33.3 mmol/l glucose supplemented with or without fatty acids (Sigma Chemical, St. Louis, Mo.; palmitic acid [16:0], palmitoleic acid [16:1], oleic acid [18:1], or a mixture of fatty acids [16:0/16:1, 16:0/18:1]). Fatty acids are dissolved at 10 mmol/L in culture medium containing 11% fatty acid-free BSA (Sigma) under nitrogen atmosphere, are shaken overnight at 37° C., are sonicated for 15 min, and are sterile filtered (stock solution). For control experiments, BSA in the absence of fatty acids is prepared, as described above. The effective FFA concentration may be determined after sterile filtration with a commercially available kit (Wako chemicals, Neuss, Germany). The calculated concentrations of non-albumin-bound FFA is derived from the molar ratio of total FFA (0.5 mmol/l) and albumin (0.15 mmol/l) using a stepwise equilibrium model reported in Spector A A, et al., Biochemistry, 10:3226–32 (1971). Unbound concentration of palmitic, palmitoleic, and oleic acids are of 0.832, 0.575, and 2.089 micromol/L, respectively, for a final concentration of 0.5 mmol/L FFA. In some experiments, islets are cultured with or without 15 micromol/L C2-ceramide, 15 micromol/L C2-Dihydroceramide (Biomol, Plymouth Meeting, Pa.), 15 micromol/L fumonisin B1 (Sigma), or tested compounds at various concentrations from 10 nmol/L to 100 micromol/L. All of them are first dissolved in prewarmed 37° C. DMSO (Fluka, Buchs, Switzerland) at 5 mmol/L. For control experiments, islets are exposed to solvent alone (0.3% DMSO).

Cell Apoptosis

As reported by Maedler, et al. (2003), the free 3-OH strand breaks resulting from DNA degradation are detected by the terminal deoxynucleotidyl transferase-mediated dUTP nick-end labeling (TUNEL) technique (Gavrieli Y, et al., *J. Cell Biol.* 119:493–501 (1992)). Islet cultures are washed with PBS, fixed in 4% paraformaldehyde (30 min, room temperature) followed by permeabilization with 0.5% Triton X-100 (4 min, room temperature), followed by the TUNEL assay, performed according to the manufacturer's instructions (In Situ Cell Death Detection Kit, AP; Boehringer Mannheim, Germany). The preparations are then rinsed with Tris-buffered saline and is incubated (10 min, room temperature) with 5-bromo-4-chloro-indolyl phosphate/nitro blue tetrazolium liquid substrate system (Sigma). For staining of the activated caspase 3, after fixation and permeabilization, islets are incubated for 2 h at 37° C. with a rabbit anti-cleaved caspase-3 antibody (1:50 dilution, D 175; Cell Signaling, Beverly, Mass.), followed by incubation (30 min, 37° C.) with a Cy3-conjugated donkey anti-rabbit antibody (1:100 dilution; Jackson ImmunoResearch Laboratories, West Grove, Pa.). Thereafter, islets are incubated with a guinea pig anti-insulin antibody as described above, followed by detection using the streptavidin-biotin-peroxidase complex (Zymed) or by a 30-min incubation with a 1:20 dilution of fluoresceinconjugated rabbit anti-guinea pig antibody (Dako). The TUNEL assay detects DNA fragmentation associated with both apoptotic and necrotic cell death; therefore, islets are also treated with a fluorescent annexin V probe (Annexin-V-FLUOS staining kit, Boehringer Mannheim) according to the manufacturer's instructions. Double staining of cells with propidium iodide and annexin V enables the differentiation of apoptotic from necrotic cells.

Example 7

Anti-Inflammatory Applications

Zucker diabetic fatty rats are sacrificed and pancreatic islets are harvested as according to Shimabukuro et al. In culture, these islets are treated with an effective amount of Tumor Necrosis Factor alpha. De novo synthesis of ceramides is evaluated by incorporation of tritiated serine, as described in Example 8. Treatment with an effective concentration of compounds presented herein results in a significantly decreased concentration of ceramide in contrast to the control group. This demonstrates the efficacy of the compounds and specific inhibition activity against SPT in general, in anti-inflammatory applications.

Example 8

Serine Palmitoyltransferase Activity

Assay A.

The assay is carried out by a minor modification of the method reported by Merrill et al., Anal. Biochem., 171: 373–381 (1988).

Frozen rat or other mammalian livers are homogenized in a standard HEPES buffer system containing DTT (5 mM), sucrose (0.25 M) and EDTA at pH 7.4. The homogenate is spun at 30 kg for 0.5 hr. and the supernatant is removed. The assay is performed using the supernatant (sufficient for 50–150 µg protein) above but with the addition of 50 µM pyridoxal, 200 µM palmitoyl-CoA, and 1 mM $^3$H-L-serine in a buffer similar to the homogenization buffer, but at pH 8.3. The radiolabeled product, 3-ketosphinganine, is extracted in $CHCl_3/CH_3OH$ and the radioactivity is counted in a liquid scintillation counter.

Inhibition of serine palmitoyl transferase is evaluated by incorporation of tritium label into the lipid product. Further demonstration of the activity of compounds in a CTLL-2 cell line can be performed using the assay described in Nakamura, S., et al., J. Biol. Chem., 271:1255–57 (1996).

Assay B.

An alternative assay for evaluating inhibition of SPT, the enzyme present in commonly cultured cells, is performed with CHO cells or a human cell line. Cells are washed three times with ice-cold phosphate-buffered saline (PBS). A total of 0.5 mL of lysis buffer [50 mM Hepes (pH 8.0) containing 5 mM ethylenediaminetetraacetic acid (EDTA) and 5 mM dithiothreitol (DTT)] is added to each dish. The cells are scraped using a rubber policeman, and are then transferred to a test tube on ice. The cell suspension is sonicated three times for 5 s at 1–2 min intervals on ice. Protein concentrations in cell homogenates are measured using a Bradford protein assay kit (Bio-Rad). To measure the SPT activity, 0.1 mL of cell homogenates are added to 0.1 mL of reaction buffer [20 mM Hepes (pH 8.0) containing 5 mM EDTA, 10 mM DTT, 50 µM pyridoxal-5'-phosphate, 0.4 mM palmitoyl CoA, 2 mM L-serine, 10 µCi of [$^3$H]serine, and test compound or standard inhibitor (myriocin). After incubation at 37° C. for 20 min with shaking, the reaction is terminated with 0.5 mL of 0.5 N NH$_4$OH containing 10 mM L-serine. The lipid products are extracted using the solvent system: 3 mL of chloroform/methanol (1:2), 25 µg of sphingosine (1 mg/mL in ethanol) as a carrier, 2 mL of chloroform, and 3.8 mL of 0.5 N NH$_4$OH. After vigorous mixing, the phases are separated by centrifugation at 2500 rpm for 5 min. The aqueous layer is removed by aspiration, and the lower chloroform layer is washed 3 times with 4.5 mL of water. The chloroform layer is transferred to a scintillation vial, and the solvent is evaporated under N$_2$ gas. The radioactivity is measured with a LS6000TA liquid scintillation counter (Beckman). Nonspecific conversion of [$^3$H] serine to chloroform-soluble species is determined by performing the assay in the absence of palmitoyl CoA. The count of the background is about one-sixth of the count of 100% activity.

Assay C.

An alternative assay using a non-chlorinated solvent modification of the Blye and Dyer lipid extraction method reported in Smedes (Smedes, F., Analyst 124:1711–18 (1999)) was employed to evaluate exemplary compounds. In this approach, the cells were washed three times with ice-cold phosphate-buffered saline and 0.5 mL of lysis buffer was added to each dish. The cells were scraped using a rubber policeman and transfer to a test tube on ice. The cell suspension was sonicated three times for 5 s at 1–2 min intervals on ice. A 0.1 mL sample of cell homogenates were added to 0.1 mL of reaction buffer in a test tube containing the appropriate concentration of test substance and 10 µCi of [$^3$H] serine. The reaction mixture was incubated at 37° C. for 20 min with shaking, and the reaction was terminated with 0.5 mL of 0.05N NH$_4$OH stop solution containing 10 mM unlabeled L-serine. Total lipids are extracted by transferring the contents of the test tube into a 15 ml centrifuge tube containing: 4.5 mL of isopropanol/cyclohexane (4:5) containing 25 µg of sphingosine (1 mg/mL in ethanol and diluted into the isopropanol/cyclohexane mixture) as a carrier. The contents were mixed vigorously and 4 mL of 0.5 N NH$_4$OH was added. The phases were separated by centrifugation at 2500 rpm for 5 min. An accurately measured portion of the organic layer (4.0 ml) was added to a scintillation vial with 1 ml of water. Ultima Gold F (5 ml) was added, the vial was vortexed and allowed to settle into separate layers. The amount of [$^3$H] serine radioactivity incorporated into lipids was quantified in a scintillation counter. Non-specific counts were determined by carrying out the assay with control samples containing no palmitoyl CoA. As shown in Table 2 below, the positive control, ISP-1 (i.e., myriocin) exhibited potent but non-selective inhibition of SPT. Exemplary compound 12 was evaluated in this assay and, as shown in Table 2, exhibited moderate activity at the doses indicated.

Table 3 provides data for exemplary compounds 23 and 24 tested in this assay at 10 nM and at 100 nM.

TABLE 2

| Test group | Counts | Std Error |
| --- | --- | --- |
| no CoA (blank) | 305 | 5 |
| No Inhibitor, t = 0 | 244 | 7 |
| No Inhibitor | 4443 | 108 |

TABLE 2-continued

| Test group | Counts | Std Error |
| --- | --- | --- |
| ISP (standard), 1 nM | 2509 | 69 |
| ISP, 10 nM | 535 | 5 |
| Compound 12, 1 nM | 4215 | 43 |
| Compound 12, 10 nM | 4118 | 69 |
| Compound 12, 100 nM | 4258 | 25 |
| Compound 12, 1 µM | 4169 | 73 |
| Compound 12, 10 µM | 4608 | 158 |
| No Inhibitor | 4483 | 153 |

TABLE 3

| Test Group | Counts | Std Error |
| --- | --- | --- |
| No cells | 598 | 18 |
| No Palm CoA | 611 | 32 |
| Control | 5816 | 348 |
| ISP 10 nM | 959 | 31 |
| 10 nM Compound 23 | 5601 | 268 |
| 100 nM Compound 23 | 5073 | 257 |
| 10 nM Compound 24 | 5763 | 131 |
| 100 nM Compound 24 | 5163 | 263 |

Example 9

Protection of Islets by an SPT Inhibitor

Islet protection by an exemplary compound was evaluated in an assay according to Eitel, K, et al (2002), and results obtained in this assay are reported below in Table 4. Rat pancreatic islets were cultured with control medium (RPMI 1640 supplemented with 10% fetal bovine serum, antibiotics and made 8% in glucose) or in medium supplemented with 1 millimolar sodium palmitate (Fatty Acid Medium) during a period of 3 days. The culture medium was changed after 2 days to an identical composition culture medium with fresh inhibitor in the appropriate wells. Cells were stained with propidium iodide (PI), washed and propidium staining of cells (as a measure of cellular DNA content) was assessed by flow cytometry. The percentage of cells having less than the normal amount of PI staining was considered to be apoptotic cells (Eitel, K, et al. (2002)).

In this assay, treatment with exemplary compound 12 appeared to fully protect cells from the fatty acid treatment in this assay and surprisingly imparts a benefit in comparison to treatment with the control medium.

TABLE 4

| Treatment | % Apoptosis | Std Dev |
| --- | --- | --- |
| Control medium | 2.40 | 0.56 |
| Fatty Acid medium | 17.60 | 5.52 |
| FA plus Compound 12 | 2.33 | 0.40 |
| myriocin -1 | 14.65 | 7.00 |

REFERENCES

Ayasolla K., et al. Free Radic. Biol. Med. 37(3):325–38 (2004)

Beattie G M, Leibowitz G, Lopez A D, Levine F, Hayek A. (2000). Protection from cell death in cultured human fetal pancreatic cells. Cell Transplant. 9, 431–8

Benjamins J A, et al. (2003). Protection of mature oligodendrocytes by inhibitors of caspases and calpains Neurochem Res. 28:143–52.

Bennett J W and Klich M. (2003). Clin Microbiol Rev. 16, 497–516.

Chen, J K, et al. (1999). The identification of myriocin-binding proteins. Chem Biol. 6, 221–35.

Clemens J. J. et al., (2004). Synthesis of benzimidazole based analogues of sphingosine-1-phosphate: discovery of potent, subtype-selective S1P4 receptor agonists. Bioorg. Med. Chem. Lett., 14: 4903–6.

Coroneos, E; Wang, Y; Panuska, J R; Templeton, D J; Kester, M. (1996). Biochem J, 31, 13–7.

Cutler R G, et al. (2004). Involvement of oxidative stress-induced abnormalities in ceramide and cholesterol metabolism in brain aging and Alzheimer's disease. Proc Natl. Acad. Sci. 101, 2070–5.

Ding, W X and Yin, X M, J. Cell. Mol. Med. 8, 445–54 (2004)

Durand, P. et al., (2000). Synthesis, 505, 6

Eitel, K., et al., (2002). Different role of saturated and unsaturated fatty acids in beta-cell apoptosis. Biochem Biophys Res Commun. 299, 853–6.

Esmon, C T. Crosstalk between inflammation and thrombosis. (2004) Maturitas. 47, 305–14

Frost R A and Lang C H. (2005). Curr Opin Clin Nutrit Metab Care, 255–263.

Fujita, T. et al. (1996). Potent Immunosuppressants, 2-alkyl-2-aminopropane-1,3-diols. J. Med. Chem. 39, 4451–59.

Gavrieli Y, et al. (1992). Identification of programmed cell death in situ via specific labeling of nuclear DNA fragmentation. *J. Cell Biol*. 119, 493–501.

Greene T and Wuts P G M. (1999) "Protective Groups in Organic Synthesis", Edition 3, Wiley, N.Y.

Hale J J, et al. (2004). Synthesis, stereochemical determination and biochemical characterization of the enantiomeric phosphate esters of the novel immunosuppressive agent FTY720. Bio-org. Med. Chem. Lett., 12, 4803–7

Hale J J, et al., (2004). Potent S1P receptor agonists replicate the pharmacologic actions of the novel immune modulator FTY720. Bioorg. Med. Chem. Lett., 14, 3351–5.

Hanada K., et al., (2003). Biochem Biophys Acta, 1632: 16–30.

Kajita, K, et al. Diabetes. Res. Clin. Pract. 66 Suppl 1, S79–83 (2004)

Kanzler S, et al. Semin Cancer Biol. 10(3):173–84 (2000)

Kiuchi M, et al. (2000). Synthesis and Immunosuppressive Activity of 2-Substituted 2-Aminopropane-1,3-diols and 2-Aminoethanols. J. Med. Chem., 43, 2946–61.

Kobayashi, S, et al. (1998). Catalytic Asymmetric Syntheses of Antifungal Sphingofungins and Their Biological Activity as Potent Inhibitors of Serine Palmitoyltransferase (SPT). J. Am. Chem. Soc. 120, 908–19.

Larock, R C. (1999). "Comprehensive Organic Transformations" $2^{nd}$ Edition, Wiley, N.Y.

Maedler, K, et al. (2003). Monosaturated Fatty Acids Prevent the Deleterious Effects of Palmitate and High Glucose on Human Pancreatic β-Cell Turnover and Function. Diabetes; 52:726–33.

McTiernan, C F, et al. Curr Cardiol Rep. 2(3), 189–97 (2000)

Merrill et al., Anal. Biochem., 171: 373–381 (1988).

Meyer, S G, et al. (2003). Biochim Biophys Acta. 1643,1–4.

Nakamura, S. et al., (1996). J. Biol. Chem., 271: 1255–7.

Oishi, T., et al. (2001). Stereoselective total synthesis of (+)-myriocin from D-mannose. Chemical Commun. 1932–3

Oberholzer J, et al. (2000). Human islet transplantation: lessons from 13 autologous and 13 allogeneic transplantations. Transplantation 69,1115–1123.

Paraskevas S, Maysinger D, Wang R, Duguid T P, Rosenberg L (2000). Cell loss in isolated human islets occurs by apoptosis. Pancreas 2000, 20, 270–6.

Pileggi A, et al. (2004). Protecting pancreatic beta-cells. IUBMB Life 56, 387–94.

Pipik, B, et al. (2004). A Preferred Synthesis of 1,2,4-Oxadiazole. Synth. Commun. 34, 1863–70

Rall L C and Roubenoff R Rheumatol 2004: 43, 1219–23.

Rosenberg L, Wang R, Paraskevas S, Maysinger D. (1999). Structural and functional changes resulting from islet isolation lead to islet cell death. Surgery. 126: 393–8.

Rother K I, Harlan D M; J Clin Invest. 2004; 114: 877–83

Sauerwald T M, et al. (2003). Study of caspase inhibitors for limiting death in mammalian cell culture. Biotechnol Bioeng. 81:329–40

Sauerwald T. M. et al. (2004). Inhibitors directed towards caspase-1 and –3 are less effective than pan caspase inhibition in preventing renal proximal tubular cell apoptosis. Nephron Exp Nephrol. 96, e39–51.

Sawada, M, et al. (2004). Cell Death Differ. 11, 997–1008.

Schimitz-Pfiffer C. et al., (1999). J. Biol. Chem., 274: 24202–10.

Seebach, D. et al. (1987). Stereoselektive Alkylierung an C(α) von Serin, Glycerinsaüre, Threonin und Weinsaüre über heterocycliische Enolate mit exocyclischer Doppelbindung. Helv. Chim. Acta. 70.1194–1216

Seidel G. et al. (2004). Iron-Catalyzed Cross-Coupling Reactions. A Scalable Synthesis of the Immmunosuppresive Agent FTY720. J. Org. Chem., 69, 3950–52.

Shimabukuro et al., (1998). J. Biol. Chem., 273: 32487–90.

Shimabukuro M., et al., (1998). Proc. Natl. Acad. Sci. USA, 95: 2498–2502.

Shinoda J, et al. (1999). Cell Signal. 11: 435–41.

Smedes, F (1999). Determination of total lipid using non-chlorinated solvents. Analyst 124, 1711–18

Spector, A A, et al. (1971). Analysis of long-chain free fatty acid binding to bovine serum albumin by determination of stepwise equilibrium constants. Biochemistry 10, 3226–32

Tisdale M J; Langenbecks Arch Surg. 2004; 389: 299–305.

Wang, Y. -F., et al. (1988). Lipase-catalyzed irreversible transesterifications using enol esters as acylating reagents: preparative enantio- and regioselective synthesis of alcohols, glycerol derivatives, sugars, and organometallics. J. Am. Chem. Soc. 110, 7200–5;

Wencker D. et al. (2003). J. Clin. Invest., 111:1497–1504

Zimmet P, et al. (2001). Nature, 414, 783–7

What is claimed is:

1. A compound, and pharmaceutically acceptable salts thereof, selected from the group consisting of:

(a) a chemical compound corresponding to Formula III:

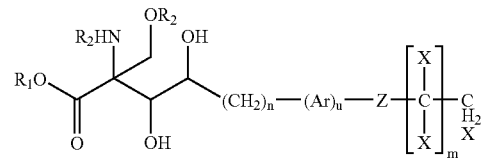

Formula III wherein:
R$_1$ is H or C$_1$ to C$_6$ alkyl;
R$_2$ is H;
n is 2 to 7;
Ar is an optionally substituted aryl or heteroaryl;
u is 1;
Z is O or CH$_2$;
each X is independently H or halogen;
m is 4 to 12;
(b) a chemical compound corresponding to Formula IIIA:

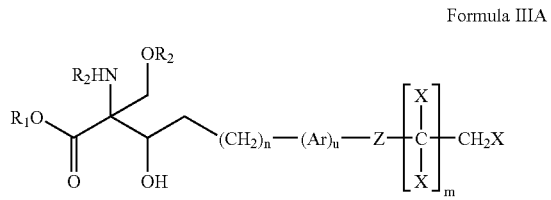

Formula IIIA wherein:
R$_1$ is H or C$_1$ to C$_6$ alkyl;
R$_2$ is H;
n is 1 to 7;
Ar is an optionally substituted aryl or heteroaryl;
u is 0 or 1;
Z is O or CH$_2$;
each X is independently H or halogen; and
m is 4 to 12; and
(c) a chemical compound corresponding to Formula IIIB:

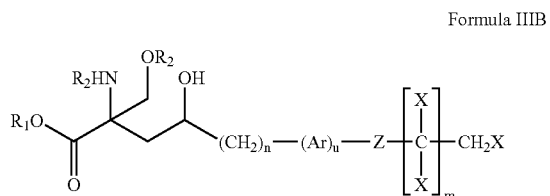

Formula IIIB wherein:
R$_1$ is H or C$_1$ to C$_6$ alkyl;
R$_2$ is H;
n is 1 to 7;
Ar is an optionally substituted aryl or heteroaryl;
u is 0 or 1;
Z is O or CH$_2$;
each X is independently H or halogen; and
m is 4 to 12.

2. A compound of claim 1, and pharmaceutically acceptable salts thereof, corresponding to Formula III:

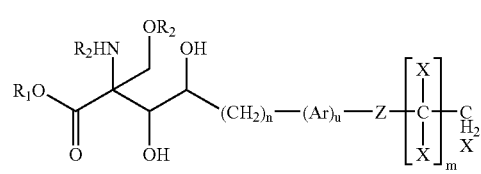

Formula III wherein:
R$_1$ is H or C$_1$ to C$_6$ alkyl;
R$_2$ is H;
n is 2 to 7;
Ar is an optionally substituted aryl or heteroaryl;
u is 1;
Z is O or CH$_2$;
each X is independently H or halogen;
m is 4 to 12.

3. A compound of claim 1, and pharmaceutically acceptable salts thereof, corresponding to Formula IIIA:

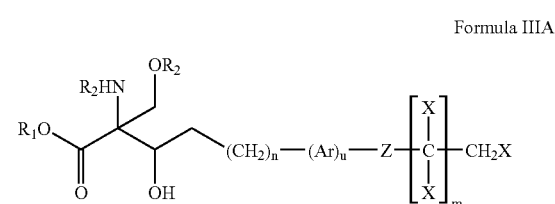

Formula IIIA wherein:
R$_1$ is H or C$_1$ to C$_6$ alkyl;
R$_2$ is H;
n 1 to 7;
Ar is an optionally substituted aryl or heteroaryl;
u is 0 or 1;
Z is O or CH$_2$;
each X is independently H or halogen; and
m is 4 to 12.

4. A compound of claim 1, and pharmaceutically acceptable salts thereof, corresponding to Formula IIIB:

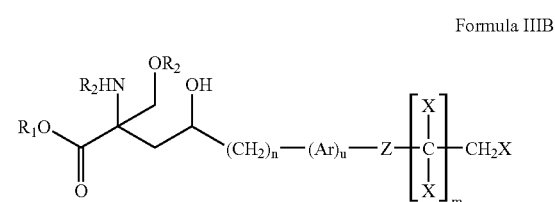

Formula IIIB wherein:
R$_1$ is H or C$_1$ to C$_6$alkyl;
R$_2$ is H;
n is 1 to 7;
Ar is an optionally substituted aryl or heteroaryl;
u is 0 or 1;
Z is O or CH$_2$;
each X is independently H or halogen; and
m is 4 to 12.

5. The compound of claim 1, wherein Ar is an optionally-substituted phenyl, pyridinyl, pyrimidyl, imidazolyl, benzimidazolyl, thiazolyl, oxazolyl, isoxazolyl, benzthiazolyl, or benzoxazolyl.

6. The compound of claim 5, wherein Ar is phenyl, pyridinyl, or oxazolyl.

7. The compound of claim 1, wherein X is a halogen.

8. The compound of claim 7, wherein each X is fluorine.

9. The compound of claim 1, wherein R$_1$ is C$_2$–C$_3$ alkyl.

10. The compound of claim 1, wherein n is 2.

11. The compound of claim 1, wherein m is 7.

12. A composition comprising the compound of claim 1 and a pharmaceutically acceptable carrier.

13. The compound of claim 2, having the structure of

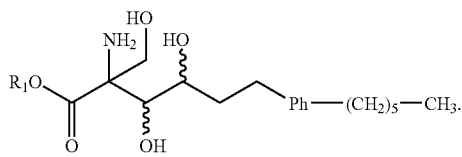

14. The compound of claim 2, having the structure of

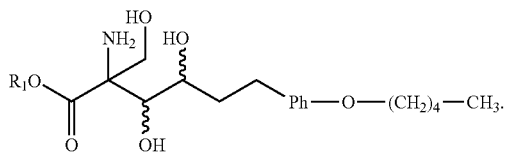

15. The compound of claim 2, having the structure of

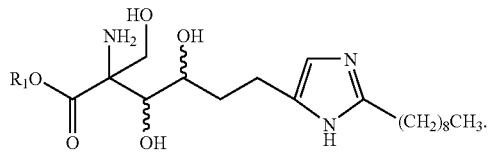

16. The compound of claim 2, having the structure of

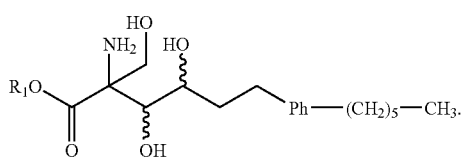

17. The compound of claim 3, having the structure of

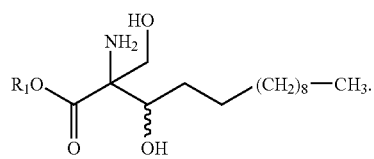

18. The compound of claim 3, having the structure of

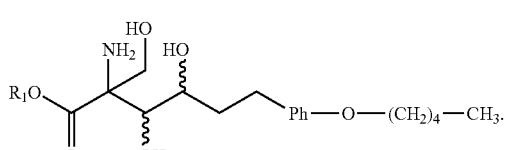

19. The compound of claim 3, having the structure of

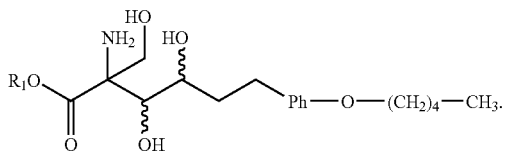

20. The compound of claim 3, having the structure of

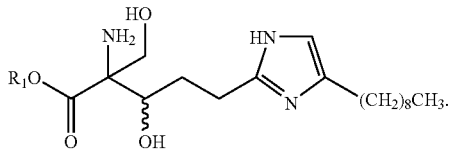

21. The compound of claim 3, having the structure of

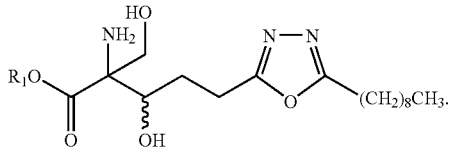

22. The compound of claim 3, having the structure of

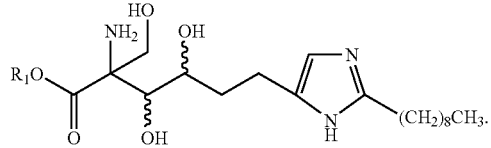

23. The compound of claim 3, having the structure of

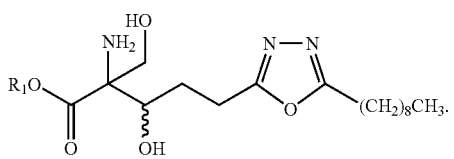

24. The compound of claim 3, having the structure of

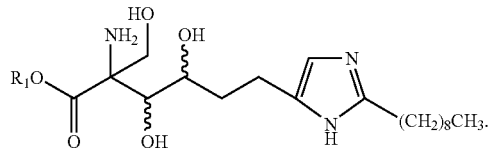

25. The compound of claim 3, having the structure of
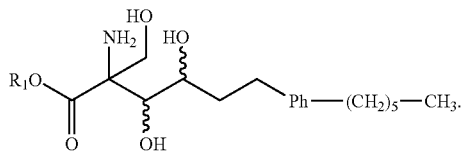
26. The compound of claim 4, having the structure of
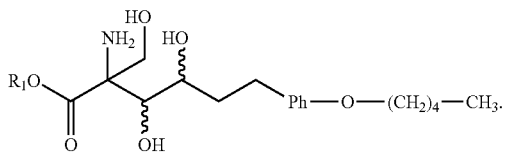
* * * * *